(12) United States Patent
Livingston et al.

(10) Patent No.: US 12,234,069 B2
(45) Date of Patent: Feb. 25, 2025

(54) RECLOSING SEPTUM CAP FOR MEDICAL SAMPLE TRANSPORT AND PROCESSING

(71) Applicant: BECTON DICKINSON AND COMPANY, Franklin Lakes, NJ (US)

(72) Inventors: Dwight Livingston, Fallston, MD (US); Ammon David Lentz, York, PA (US); Sharon Virginia LaMont Leitch, Shrewsbury, PA (US); Gary F. Hershner, Red Lion, PA (US); Daniel Justin Lohan, Glen Rock, PA (US); Joseph Kelleher, Baltimore, MD (US); Elisabeth Lily Sooklal, Reisterstown, MD (US)

(73) Assignee: BECTON DICKINSON AND COMPANY, Franklin Lakes, NJ (US)

( * ) Notice: Subject to any disclaimer, the term of this patent is extended or adjusted under 35 U.S.C. 154(b) by 489 days.

(21) Appl. No.: 17/543,858

(22) Filed: Dec. 7, 2021

(65) Prior Publication Data

US 2022/0089338 A1 Mar. 24, 2022

Related U.S. Application Data

(63) Continuation of application No. PCT/US2020/037408, filed on Jun. 12, 2020.
(Continued)

(51) Int. Cl.
*B65D 51/00* (2006.01)
*A61B 10/00* (2006.01)
*B01L 3/00* (2006.01)

(52) U.S. Cl.
CPC ........ *B65D 51/002* (2013.01); *A61B 10/0096* (2013.01); *B01L 3/50825* (2013.01);
(Continued)

(58) Field of Classification Search
CPC .............. B65D 51/002; A61B 10/0096; B01L 3/50825; B01L 2200/141; B01L 2300/044; B01L 2300/123
(Continued)

(56) References Cited

U.S. PATENT DOCUMENTS 1,879,820 A 9/1932 Perry
3,682,315 A 8/1972 Haller
(Continued)

FOREIGN PATENT DOCUMENTS

CN 1294675 A 5/2001
CN 1495420 A 5/2004
(Continued)

OTHER PUBLICATIONS

Danone Design dated May 24, 1997.
(Continued)

*Primary Examiner* — Nathaniel T Woodward
(74) *Attorney, Agent, or Firm* — Botos Churchill IP Law LLP

(57) ABSTRACT

A pierceable cap may be used for containing sample specimens. The pierceable cap may prevent escape of sample specimens before transfer with a transfer device. The pierceable cap may fit over a vessel. An access port in the shell of the pierceable cap may allow passage of a transfer device through the pierceable cap. The shell receives a septum that has four half dome indentations, each indentation defining a quadrant of the septum interior. The indentations are separated by the septum floor which extends along respective first and second diameters of the septum and intersect at approximately ninety degrees. The half dome indentations guide a transfer device to the partially slitted portion of the septum floor.

19 Claims, 30 Drawing Sheets

Related U.S. Application Data

(60) Provisional application No. 62/861,043, filed on Jun. 13, 2019.

(52) U.S. Cl.
CPC ... *B01L 2200/141* (2013.01); *B01L 2300/044* (2013.01); *B01L 2300/123* (2013.01)

(58) Field of Classification Search
USPC .................................................. 73/864.84
See application file for complete search history.

(56) References Cited

U.S. PATENT DOCUMENTS

| | | | |
|---|---|---|---|
| 4,545,497 A | 10/1985 | Martha | |
| 4,626,245 A | 12/1986 | Weinstein | |
| 4,924,923 A | 5/1990 | Boehmer et al. | |
| D323,555 S | 1/1992 | Rasmusson | |
| 5,269,763 A * | 12/1993 | Boehmer | A61M 39/0606 604/167.04 |
| 5,366,893 A | 11/1994 | Stevens et al. | |
| 5,370,252 A | 12/1994 | Parsons et al. | |
| 5,706,860 A | 1/1998 | Gonyea | |
| 6,171,287 B1 | 1/2001 | Lynn et al. | |
| 6,475,774 B1 | 11/2002 | Gupta | |
| 6,478,360 B1 | 11/2002 | Reutter | |
| 6,562,300 B2 | 5/2003 | Rosen et al. | |
| D480,640 S | 10/2003 | Oyama et al. | |
| D502,046 S | 2/2005 | Isler et al. | |
| D516,913 S | 3/2006 | Lamasney | |
| D582,032 S | 12/2008 | Bizup et al. | |
| D586,905 S | 2/2009 | Fisher et al. | |
| D602,164 S | 10/2009 | Speth et al. | |
| 7,795,036 B2 | 9/2010 | Johnson et al. | |
| D647,627 S | 10/2011 | Wilkinson | |
| 8,387,810 B2 | 3/2013 | Livingston et al. | |
| 8,387,811 B2 | 3/2013 | Livingston et al. | |
| D690,433 S | 9/2013 | Karpiloff et al. | |
| D717,430 S | 11/2014 | Shiraishi et al. | |
| D738,210 S | 9/2015 | Tanner | |
| 9,545,632 B2 | 1/2017 | Lentz et al. | |
| D806,241 S | 12/2017 | Swinney et al. | |
| D824,027 S | 7/2018 | Flores et al. | |
| D829,896 S | 10/2018 | Py | |
| D834,532 S | 11/2018 | Maroney et al. | |
| D852,375 S | 6/2019 | Druga et al. | |
| D859,686 S | 9/2019 | Charm | |
| D886,320 S | 6/2020 | Bruemmer et al. | |
| D887,577 S | 6/2020 | Shor et al. | |
| 2001/0039058 A1 | 11/2001 | Iheme et al. | |
| 2009/0048534 A1 | 2/2009 | Triva | |
| 2009/0257922 A1 | 10/2009 | Baker | |
| 2014/0008321 A1 | 1/2014 | Lentz et al. | |
| 2014/0011292 A1 | 1/2014 | Lentz et al. | |

FOREIGN PATENT DOCUMENTS

| | | | |
|---|---|---|---|
| CN | 107074415 A | 8/2017 | |
| CN | 109292248 A | 2/2019 | |
| CN | 213567462 U | 6/2021 | |
| EP | 2144700 A2 | 1/2010 | |
| EP | 3241782 A1 * | 11/2017 | ............... B01L 3/56 |
| JP | H01-168462 U | 11/1989 | |
| KR | 200177951 Y1 | 4/2000 | |
| KR | 30-0271463 | 2/2001 | |
| KR | 30-0282379 | 10/2001 | |
| WO | 0069389 A2 | 11/2000 | |
| WO | 2008130929 A2 | 10/2008 | |
| WO | 2012112505 A2 | 8/2012 | |

OTHER PUBLICATIONS

International Design Registration, Hague Express Jun. 6, 1997.
International Search Report and Written Opinion issued in PCT application No. PCT/US2020/037408 on Sep. 25, 2020.
Extended European Search Report for European Patent Application No. 12746500 dated Sep. 24, 2015.
Extended European Search Report for European Patent Application No. 20822092.1 dated Jun. 14, 2023.
International Search Report and Written Opinion issued in PCT application No. PCT/US2012/024993 on Sep. 27, 2012.
Japanese Office Action issued in corresponding JP application No. 2021-573957 on May 21, 2024, pp. 12.
Chinese Office Action and Search Report issued in corresponding CN application No. 2020800431307 on Jun. 21, 2024.
Second Office Action issued in corresponding CN application No. 2020800431307 on Nov. 29, 2024., pp. 13.

\* cited by examiner

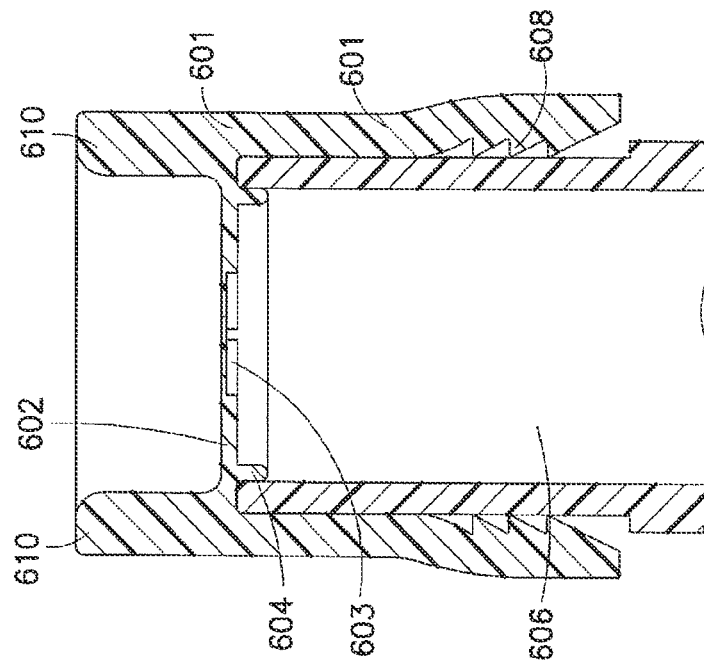
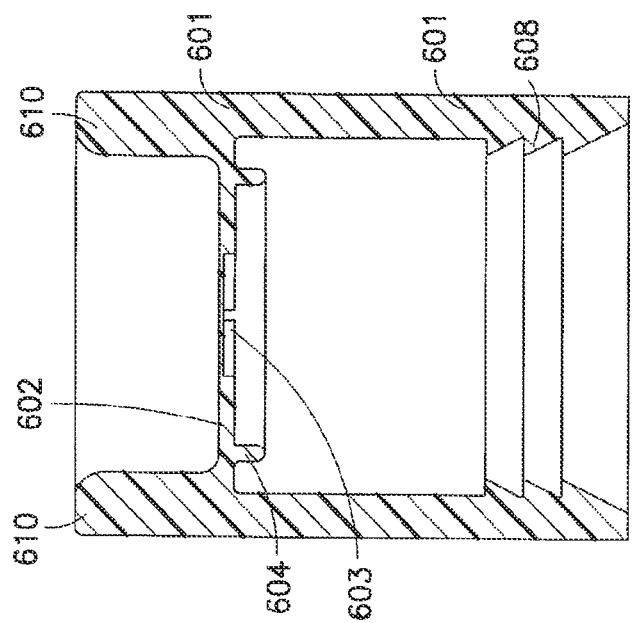
FIG. 11A
FIG. 11B

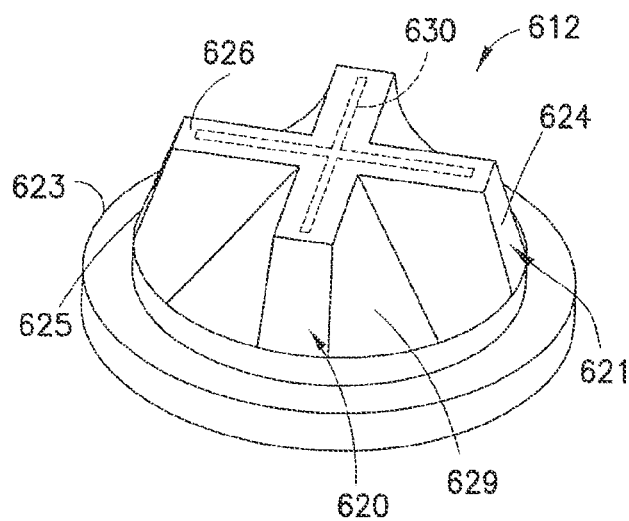
FIG.12
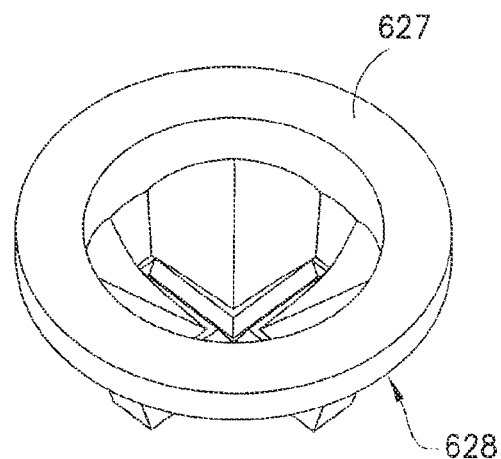
FIG.13
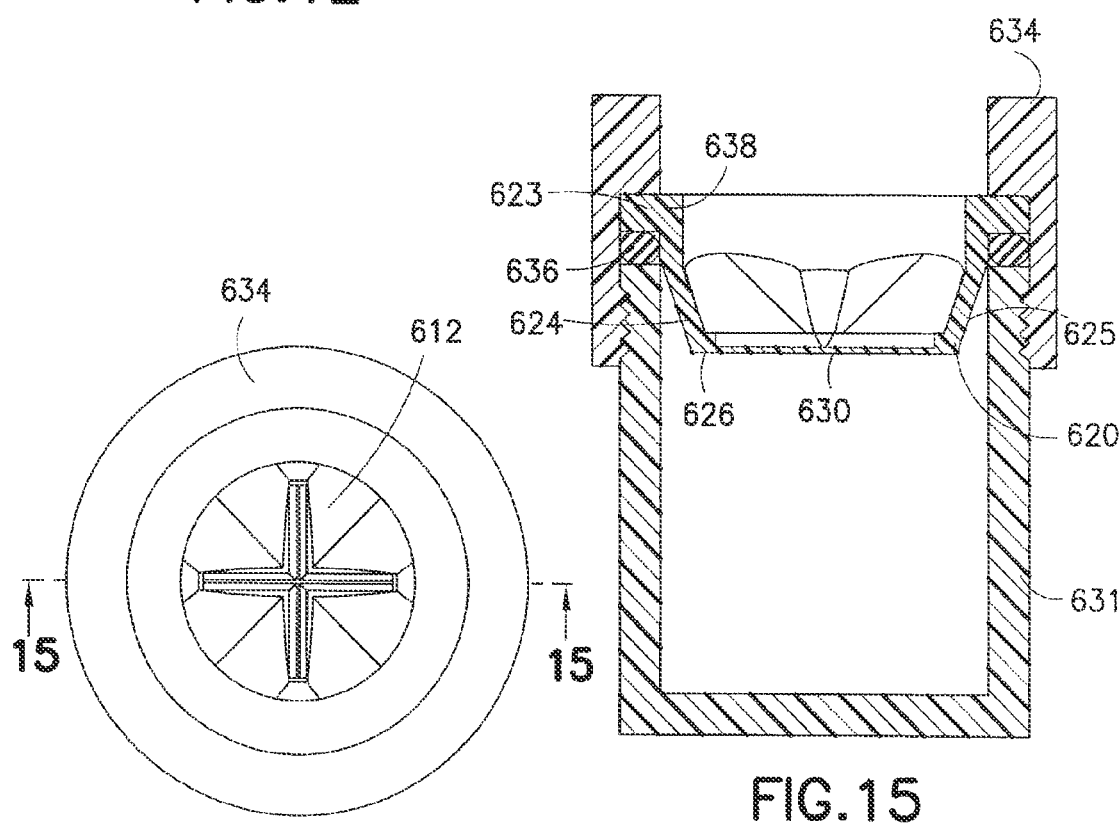
FIG.14
FIG.15

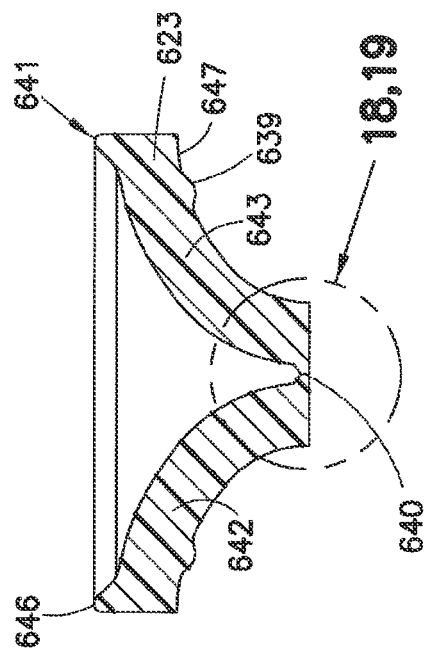
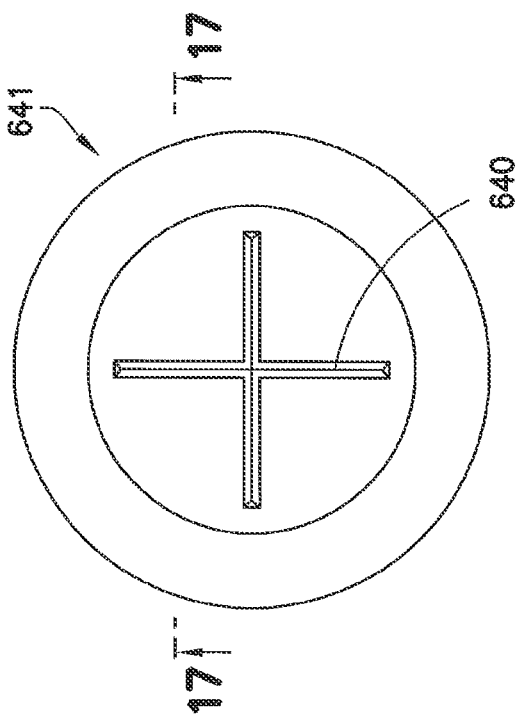
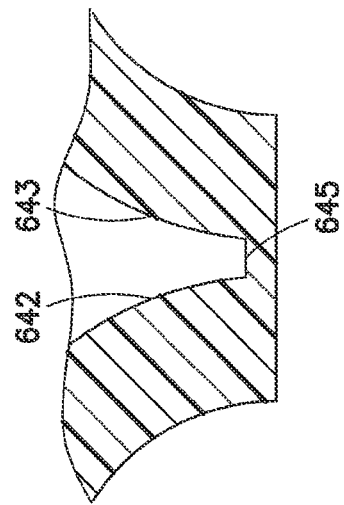
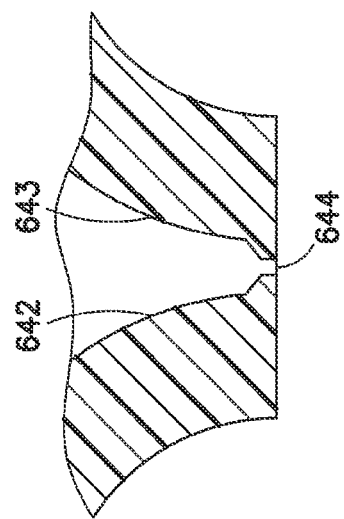

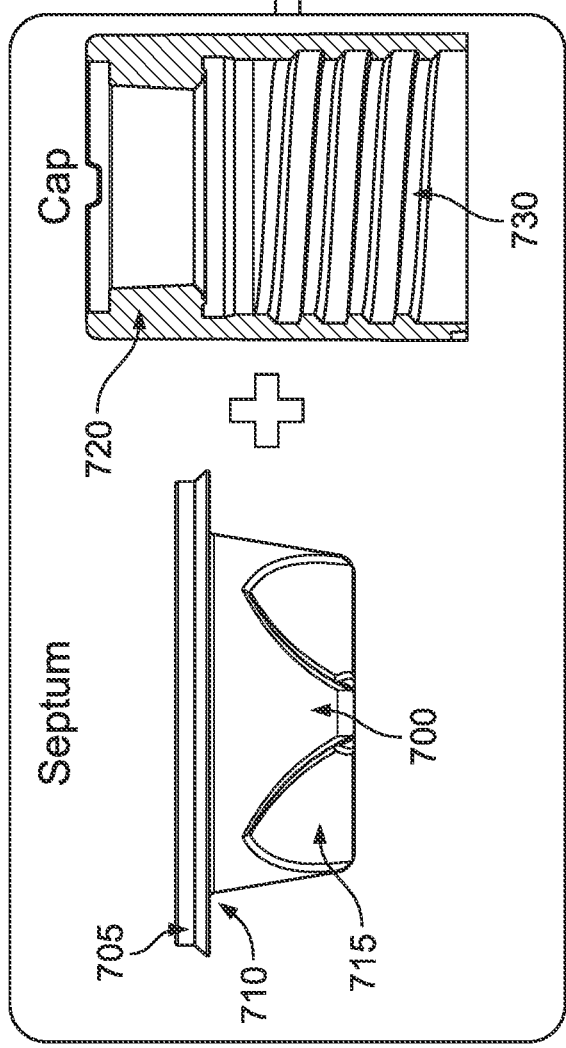
FIG. 22A
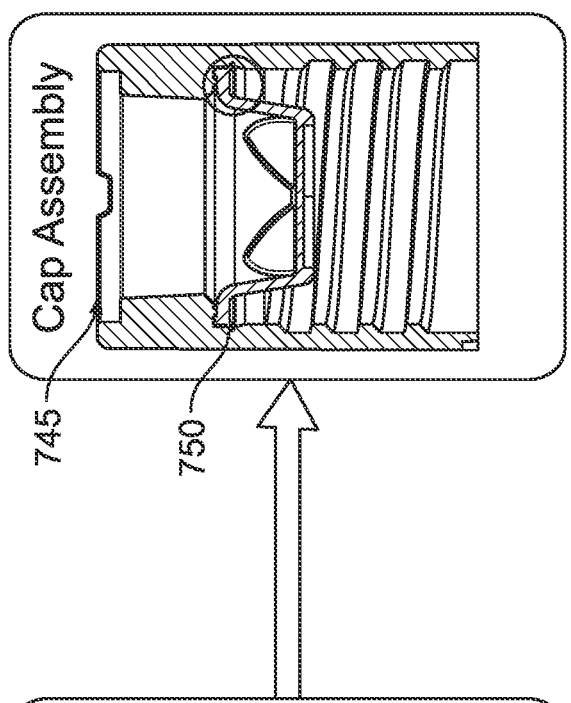
FIG. 22B
FIG. 22C
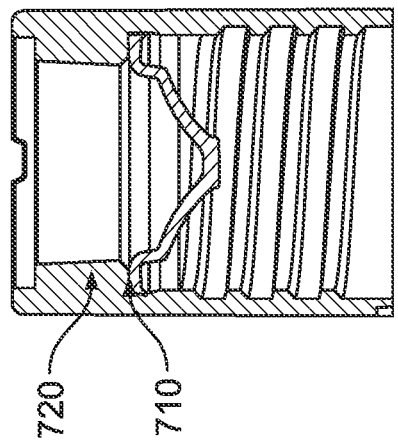
FIG. 22D
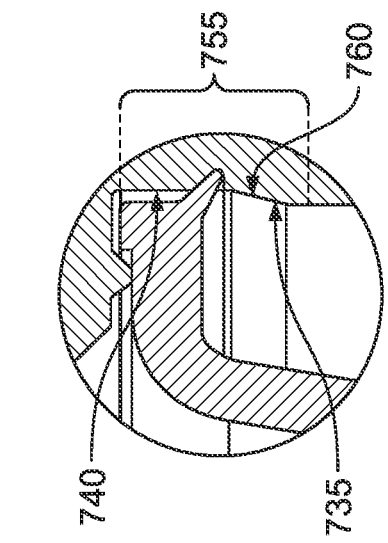
FIG. 22E

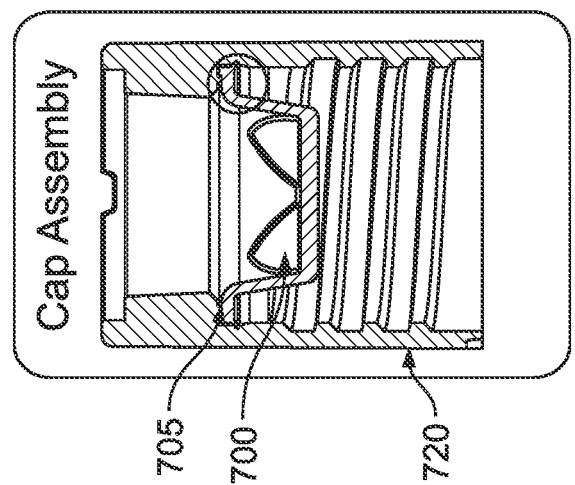
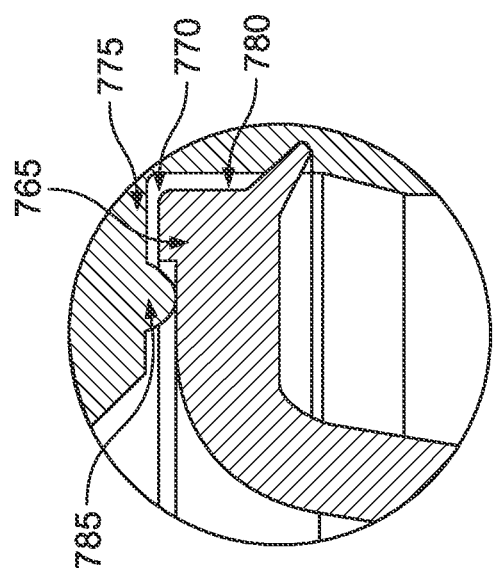
FIG. 22F

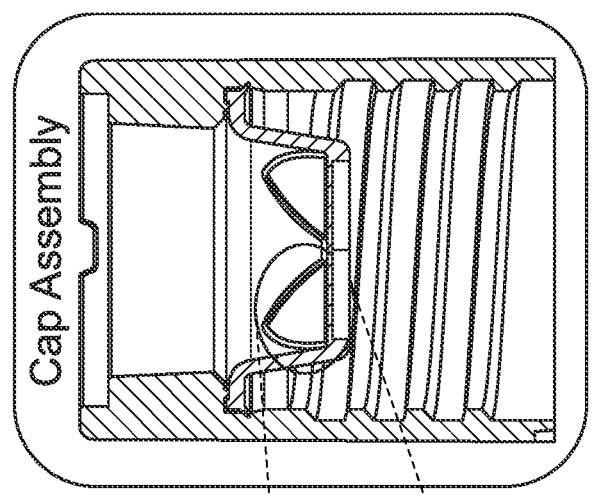
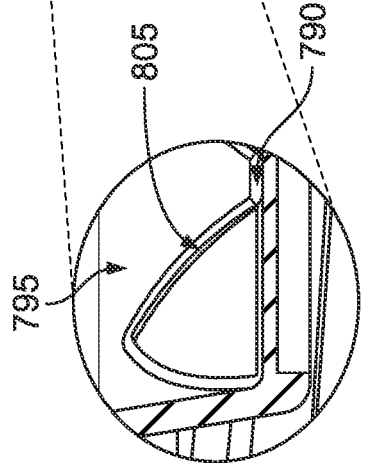
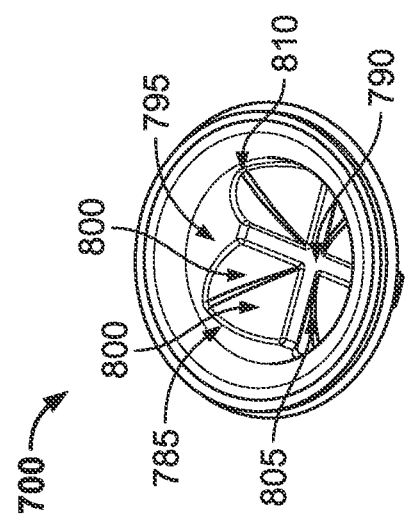
FIG. 23B
FIG. 23A

RECLOSING SEPTUM CAP FOR MEDICAL SAMPLE TRANSPORT AND PROCESSING

CROSS REFERENCE TO RELATED APPLICATIONS

ThisThe present application is a continuation of International Application No. PCT/US20/3408, filed Jun. 12, 2020, published in English, which claims the priority and benefit of U.S. Provisional Application No. 62/861,043 filed Jun. 13, 2019, which is hereby incorporated by reference. Commonly owned U.S. patent application Ser. No. 11/785,144, filed Apr. 16, 2007, entitled "Pierceable Cap" which issued as U.S. Pat. No. 8,387,810 on Mar. 5, 2013 and Ser. No. 11/979,713, filed Nov. 7, 2007, entitled "Pierceable Cap" which issued as U.S. Pat. No. 8,387,811 on Mar. 5, 2013 are related to this application and incorporated by reference herein in their entirety. International Application PCT/US2012/024993 (published as WO2012/112505) filed on Feb. 14, 2012, which claims priority to U.S. Provisional Application Ser. No. 61/442,676 (filed Feb. 14, 2011) and 61/442,634 (filed Feb. 14, 2011), are also incorporated by reference in their entirety. U.S. Pat. No. 9,545,632, which issued on Jan. 17, 2017 from application Ser. No. 13/985,177 filed Feb. 14, 2012 and U.S. patent application Ser. No. 15/372,021 filed on Dec. 7, 2016 are entitled "Pierceable Cap" and are also commonly owned and incorporated by reference herein in their entirety.

BACKGROUND OF THE INVENTION

Combinations of caps and vessels are commonly used for receiving and storing specimens. In particular, biological and chemical specimens may be analyzed to determine the existence of a particular biological or chemical agent. Types of biological specimens commonly collected and delivered to clinical laboratories for analysis may include blood, urine, sputum, saliva, pus, mucous, cerebrospinal fluid, and others. Since these specimen types may contain pathogenic organisms or other harmful compositions, it is important to ensure that vessels are substantially leak-proof during use and transport. Substantially leak-proof vessels are particularly critical in cases where a clinical laboratory and a collection facility are separate.

To prevent leakage from the vessels, caps are typically screwed, snapped or otherwise frictionally fitted onto the vessel, forming an essentially leak-proof seal between the cap and the vessel. In addition to preventing leakage of the specimen, a substantially leak-proof seal formed between the cap and the vessel may reduce exposure of the specimen to potentially contaminating influences from the surrounding environment. A leak-proof seal can prevent introduction of contaminants that could alter the qualitative or quantitative results of an assay as well as preventing loss of material that may be important in the analysis.

While a substantially leak-proof seal may prevent specimen seepage during transport, physical removal of the cap from the vessel prior to specimen analysis presents another opportunity for contamination. When removing the cap, any material that may have collected on the under-side of the cap during transport may come into contact with a user or equipment, possibly exposing the user to harmful pathogens present in the sample. If a film or bubbles form around the mouth of the vessel during transport, the film or bubbles may burst when the cap is removed from the vessel, thereby disseminating specimen into the environment. It is also possible that specimen residue from one vessel, which may have transferred to the gloved hand of a user, will come into contact with specimen from another vessel through routine or careless removal of the caps. Another risk is the potential for creating a contaminating aerosol when the cap and the vessel are physically separated from one another, possibly leading to false positives or exaggerated results in other specimens being simultaneously or subsequently assayed in the same general work area through cross-contamination.

Concerns with cross-contamination are especially acute when the assay being performed involves nucleic acid detection and an amplification procedure, such as the well-known polymerase chain reaction (PCR) or a transcription based amplification system (TAS), such as transcription-mediated amplification (TMA) or strand displacement amplification (SDA). Since amplification is intended to enhance assay sensitivity by increasing the quantity of targeted nucleic acid sequences present in a specimen, transferring even a minute amount of specimen from another container, or target nucleic acid from a positive control sample, to an otherwise negative specimen could result in a false-positive result.

A pierceable cap can relieve the labor of removing screw caps prior to testing, which in the case of high throughput instruments, may be considerable. A pierceable cap can minimize the potential for creating contaminating specimen aerosols and may limit direct contact between specimens and humans or the environment. Certain caps with only a frangible layer, such as foil, covering the vessel opening may cause contamination by jetting droplets of the contents of the vessel into the surrounding environment when pierced. When a sealed vessel is penetrated by a transfer device, the volume of space occupied by a fluid transfer device will displace an equivalent volume of air from within the collection device. In addition, temperature changes can lead to a sealed collection vessel with a pressure greater than the surrounding air, which is released when the cap is punctured. Such air displacements may release portions of the sample into the surrounding air via an aerosol or bubbles. It would be desirable to have a cap that permits air to be transferred out of the vessel in a manner that reduces or eliminates the creation of potentially harmful or contaminating aerosols or bubbles.

Other existing systems have used absorptive penetrable materials above a frangible layer to contain any possible contamination, but the means for applying and retaining this material adds cost. In other systems, caps may use precut elastomers for a pierceable seal, but these caps may tend to leak. Other designs with valve type seals have been attempted, but the valve type seals may cause problems with dispense accuracy.

Ideally, a cap may be used in both manual and automated applications, and would be suited for use with pipette tips made of a plastic material.

Generally, needs exist for improved apparatus and methods for sealing vessels with caps during transport, insertion of a transfer device, resealing and storage of samples after initial testing, additional transfer of sample from the vessel after storage, or transfer of samples. Improvements in replacement caps that have already been accessed, which may need to be sealed and stored for future access is also described.

SUMMARY OF THE INVENTION

Described herein is a reclosing septum cap for medical sample transport and processing. Embodiments of the present invention solve some of the problems and/or overcome many of the drawbacks and disadvantages of the prior art by providing an apparatus and method for sealing vessels with pierceable caps that reseal when a transfer device that is inserted through the seal for sample transport into or from the vessel is withdrawn from insertion through the septum cap.

Certain embodiments of the invention accomplish this by providing a pierceable cap apparatus including a shell, an access port in the shell for allowing passage of at least part of a transfer device through the access port, wherein the transfer device transfers a sample specimen, a lower frangible layer disposed across the access port for preventing transfer of the sample specimen through the access port prior to insertion of the at least part of the transfer device, one or more upper frangible layers disposed across the access port for preventing transfer of the sample specimen through the access port after insertion of the at least part of the transfer device through the lower frangible layer, one or more extensions between the lower frangible layer and the one or more upper frangible layers, and wherein the one or more extensions move and pierce the lower frangible layer upon application of pressure from the transfer device.

In embodiments of the present invention the lower frangible layer may be coupled to the one or more extensions. The one or more upper frangible layers may contact a conical tip of a transfer device during a breach of the lower frangible layer.

Embodiments of the present invention may include one or more upper frangible layers that are peripherally or otherwise vented.

In embodiments of the present invention the upper frangible layer and the lower frangible layer may be foil or other materials. The upper frangible layer and the lower frangible layer may be constructed of the same material and have the same dimensions. Either or both of the upper frangible layer and the lower frangible layer may be pre-scored.

Embodiments of the present invention may include an exterior recess within the access port and between a top of the shell and the one or more extensions.

The one or more upper frangible layers may be offset from the top of the shell or may be flush with a top of the shell.

A peripheral groove for securing the lower frangible layer within the shell may be provided. A gasket for securing the lower frangible layer within the shell and creating a seal between the pierceable cap and a vessel may be provided.

In embodiments of the present invention the movement of the one or more extensions may create airways for allowing air to move through the access port. The one or more upper frangible layers may be peripherally vented creating a labyrinth-like path for the air moving through the access port.

Alternative embodiments of the present invention may include a shell, an access port through the shell, a lower frangible layer disposed across the access port, an upper frangible layer disposed across the access port, and one or more extensions between the lower frangible layer and the upper frangible layer wherein the one or more extensions are coupled to walls of the access port by one or more coupling regions.

In another alternate embodiment, a single frangible seal is seated within a shell. In these embodiments, the seal is configured to address the problems that derive from the fact that the volume of air in the vessel displaced by the transfer device (e.g., a pipette) can be larger than the headspace in the vessel containing the specimen. In certain embodiments, such seals are made of a material that forms a seal around the transfer device when the seal is initially pierced (to prevent the backsplash of fluid from the vessel during piercing) but allows for venting from the vessel only after the initial piercing. In other embodiments, the frangible seal is not required to seal around the transfer device to prevent aerosolization upon piercing, for the narrowing portion of the seal itself serves to prevent the undesired backsplash as described in further detail below. For venting, the seal is provided with a preferably asymmetric tearable portions that are disposed on structural ribs on the underside of the seal. However, symmetric tearable portions are also contemplated. The weakened portions tear in a manner that does not permit venting upon the initial pierce, but, as the transfer device is advanced through the seal, venting will occur because of the asymmetry in the tearable portion. The design leverages the use of a tapered transfer device, wherein the tip (distal portion) of the transfer device has the smallest diameter. The increasing thickness of the transfer device causes the weakened portions to tear, and those tears permit desired venting during transfer, but not during the initial piercing of the frangible seal. During initial piercing, venting from the vessel can only occur through the transfer device, and not through the frangible seal. In an alternate embodiment, the seal and shell are a unitary structure as contemplated herein.

In another alternative embodiment, the frangible seal is configured so that its circumference narrows as it extends into the vessel from the cap in which it is seated. This narrowing serves a two-fold purpose of guiding the transfer device to the weakened portion for insertion through the seal and (as noted above) preventing specimen backsplash during the initial piercing. The narrowing portion may have a circumferential band, either integral to the seal or configured as an O-ring, that exerts an upward pressure on the narrowing portion, causing it to close up when the transfer device is removed from the vessel, working to substantially reseal the transfer device after sample transfer. The walls of this narrowing section may also close on each other after the initial puncture to effect resealing of the closure.

Embodiments of the present invention may also include a method of piercing a cap including providing a pierceable cap comprising a shell, an access port through the shell, a lower frangible layer disposed across the access port, an upper frangible layer disposed across the access port, and one or more extensions between the lower frangible layer and the upper frangible layer wherein the one or more extensions are coupled to walls of the access port by one or more coupling regions, inserting a transfer device into the access port, applying pressure to the one or more upper frangible layers to breach the one or more upper frangible layers, applying pressure to the one or more extensions with the transfer device wherein the one or more extensions rotate around the one or more coupling regions to contact and breach the lower frangible layer, and further inserting the transfer device through the access port.

In additional embodiments, the pierceable cap may contain a shell adapted to couple with a sample vessel, and that shell may also contain an access port in the shell, which allows for passage of a fluid transfer device, such as a pipette. The cap may also contain a penetrable seal having walls, wherein those walls form a bottom surface having an openable slitted portion adapted to be closed when the pierceable cap is fastened to a sample vessel. Bottom, as used herein, is the vessel side of the septum. Top, as used herein, is the cap side of the septum.

In other embodiments, the pierceable caps may contain an annular ring from which extend the walls with lower surfaces having protuberances that may be configured to be compressed against a sample vessel when the pierceable cap is fastened to the sample vessel. This compression occurs as the cap is screwed onto the vessel and causes the openable slitted portion to close. The openable slitted portion may be a tearable slitted portion or an unjoined slit.

In yet another embodiment, a pierceable cap may have an elastomeric shell containing locking structures for securing the shell to a vessel, and may also have a resilient access port in the shell for allowing passage of at least part of a transfer device. The cap may also contain a frangible layer with cross slits disposed across the access port which may prevent transfer of the sample specimen through the access port before insertion of at least part of the transfer device.

The frangible layer may also have ribbed portions extending both inwardly and downwardly into the vessel which terminate in a bottom surface having weakened portions disposed thereon. This bottom surface is referred to herein as the septum floor. These cross slits may be tearable webbed cross-slits or unjoined cross slits. Other slit configurations include scored portions where the scoring is not through the entire thickness of the of the pierceable septum. These partially scored portions are referred to as partial slits herein. Partial slits should be oriented with the slits on the bottom surface of the septum extending upward and only partially through the thickness of the septum floor. The cap may also contain an O-ring configured on the shell to be disposed between the shell and a sample vessel, when the shell is seated on the sample vessel. The frangible layer and the O-ring may be one piece, and the ribbed portions of the frangible layer may serve to guide the transfer device to the slitted portions on insertion, and close upon each other when the transfer device is removed. This structural arrangement allows the slitted portion to be openable.

In one embodiment, the frangible seal is a septum made of an elastomeric material that sits within the cap. The septum is engaged with the tube onto which the cap is fastened. Typically, the cap is threaded, as is the tube. The cap is fastened onto to tube by threaded engagement. The septum is configured to have a retention ring that is at least partially received by a complementary recess in the cap. This recess is bordered by the cap wall on one side and a rib extending from a lateral from the cap wall. A projection from the septum retention ring fits in a gap defined by the cap wall and the rib. Fitting the retention ring projection into this recess in the lateral extension from the cap wall ensures that the septum remains in place when the pipette is inserted into or removed from the septum.

In this embodiment the septum retention ring also includes a laterally extending barb that extends toward the cap wall. When the cap with the septum is assembled onto the mouth of the tube, the barb is deformed and lodges between the outer wall of the tube mouth and the cap. The barb holds the septum in the cap when the cap is not fastened onto the tube. The inner wall of the cap has a slightly wider inner diameter in the barb region and tapers to a slightly smaller inner diameter so that the barb is received into the slightly wider inner diameter of the cap and retained in the cap by the slightly narrower inner diameter of the cap.

In this embodiment, the tearable or weakened portion of the septum through which the pipette passes to aspirate sample from or dispense sample into the tube is defined by four half dome structures that extend from the perimeter of the septum into the interior of the septum. In one embodiment the half-dome structure is configured as a pointed arch intersecting with one half on a second pointed arch. The septum wall is configured as two sloping triangles bifurcated by the half arch. The arch structures force the septum closed after the pipette is retracted from engagement with the septum.

Also described herein is a method for piercing a septum cap. According to the method, a vessel with a pierceable cap is obtained. The pierceable cap has a shell, and an access port in the shell adapted to allow passage of at least part of a transfer device through the access port; the septum seal comprising a collar and a plurality of half-domed indentations extending from a perimeter of the septum toward the center thereof. The indentations extend inwardly and downwardly toward a substantially planar septum floor. The septum floor has a thickness, wherein the shell is adapted to receive the septum seal and wherein the substantially planar septum floor has a slitted portion that extends only partially through the thickness of the septum floor. The pipette tip is positioned over the septum seal. The pipette tip is advanced into contact with the septum floor after which the pipette tip is further advanced through the septum floor such that the pipette tip advances through an unslitted portion in the septum floor thickness initially and then further advances through the slitted portion. According to the method the access port has a first frangible layer positioned in the access port. The pipette tip is advanced through the frangible layer before the pipette tip is advanced through the septum floor.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE INVENTION

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 11a is a cross section of a pierceable cap with integrated sealing rings.

FIG. 11b is a cross section of the pierceable cap from FIG. 11a assembled with a sample vessel.

FIG. 12 is a perspective bottom view of a ribbed frangible seal.

FIG. 13 is a perspective top view of a ribbed frangible seal.

FIG. 14 is a top view of a ribbed frangible seal assembled with a sample vessel.

FIG. 15 is a cross section view of a ribbed frangible seal assembled with a sample vessel.

FIG. 16 is a top view of a shell and seal present in one embodiment of the present invention.

FIG. 17 is a cross section view of a shell and seal present in one embodiment of the present invention.

FIG. 18 is an exploded view of FIG. 17 depicting a seal with an opening on the bottom surface.

FIG. 19 is an exploded view of an alternate embodiment of FIG. 17 depicting a seal with a frangible membrane.

FIG. 22A illustrates a septum according to one embodiment of the invention.

FIG. 22B illustrates a cap adapted to receive the septum of FIG. 22A.

FIG. 22C illustrates the septum of FIG. 22A assembled with the cap of FIG. 22B.

FIG. 22D is a detail view of a portion of the septum collar received into the cap.

FIG. 22E is a detail view of a gap in a laterally extending surface of the cap that receives a projection from the septum retention ring.

FIG. 22F is a detail view of the septum of FIG. 22A disposed in the cap assembly.

FIG. 23A is a perspective view of the septum in FIG. 22 A.

FIG. 23B is detail view of a cross section of the septum arch illustrated in FIG. 23A.

DETAILED DESCRIPTION

Figure 1A:
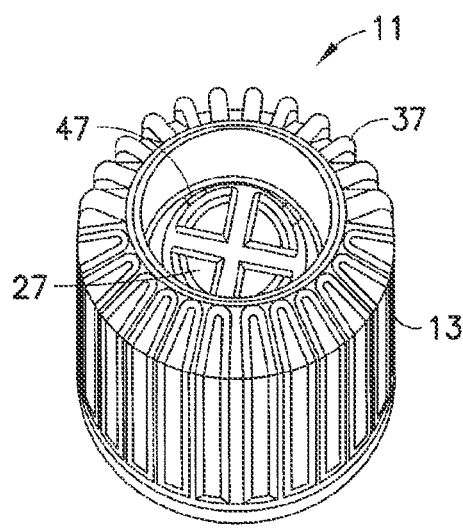
FIG. 1A is a perspective view of a pierceable cap with a diaphragm frangible layer.
Figure 1B:
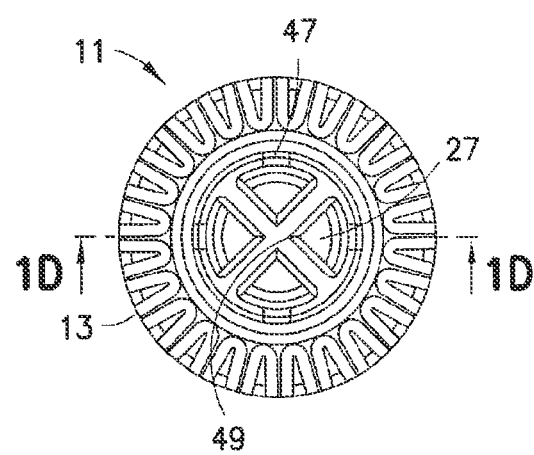
FIG. 1B is a top view of the pierceable cap of FIG. 1A.
Figure 1C:
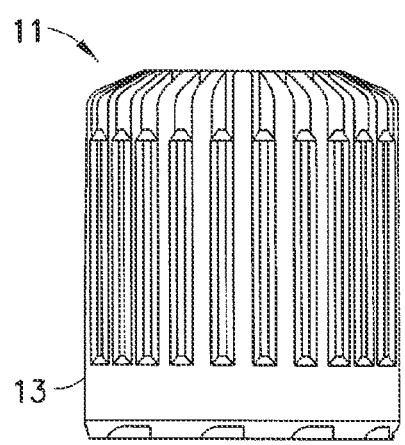
FIG. 1C is a side view of the pierceable cap of FIG. 1A.
Figure 1D:
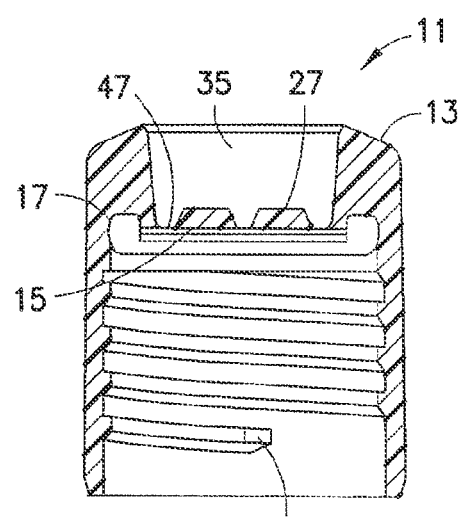
FIG. 1D is a cross-sectional view of the pierceable cap of FIG. 1A.
Figure 1E:
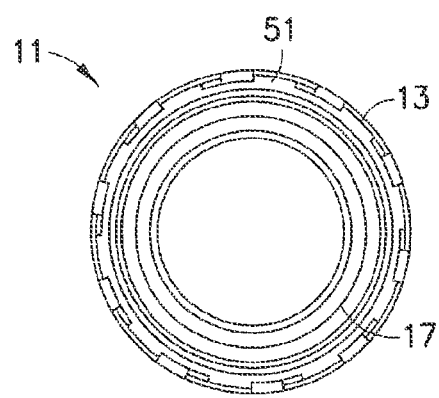
FIG. 1E is a bottom view of the pierceable cap of FIG. 1A pierced with the diaphragm (not shown).
Figure 1F:
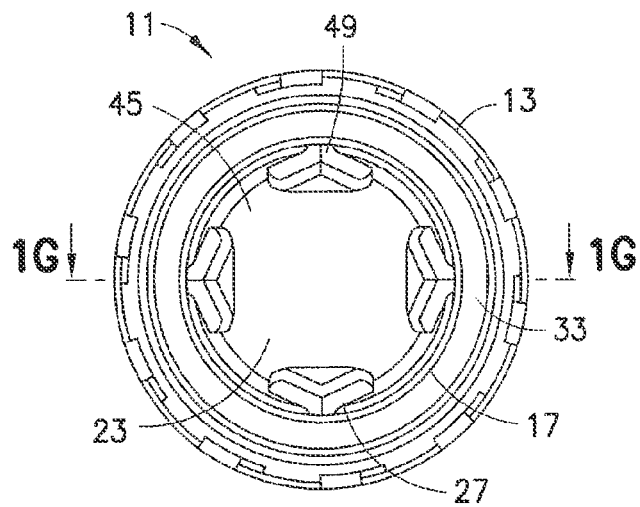
FIG. 1F is a top view as molded of the pierceable cap of FIG. 1A.
Figure 1G:
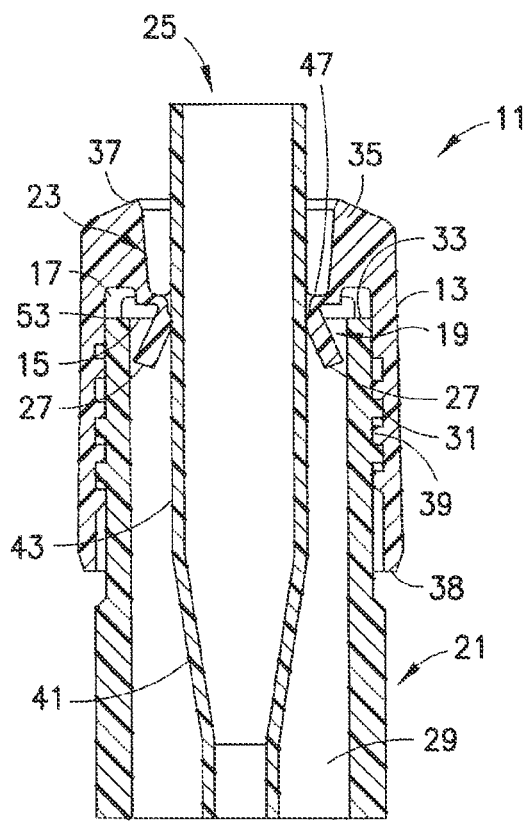
FIG. 1G is a cross-sectional view of a pierceable cap of coupled to a vessel with a pipette tip inserted through the cap.

Some embodiments of the invention are discussed in detail below. While specific example embodiments may be discussed, it should be understood that this is done for illustration purposes only. A person skilled in the relevant art will recognize that other components and configurations may be used without parting from the spirit and scope of the invention.

Embodiments of the present invention may include a pierceable cap for closing a vessel containing a sample specimen. The sample specimen may include diluents for transport and testing of the sample specimen. A transfer device, such as, but not limited to, a pipette, may be used to transfer a precise amount of sample from the vessel to testing equipment. A pipette tip may be used to pierce the pierceable cap. A pipette tip is preferably plastic, but may be made of any other suitable material. Scoring the top of the vessel can permit easier piercing. The sample specimen may be a liquid patient sample or any other suitable specimen in need of analysis.

A pierceable cap of the present invention may be combined with a vessel to receive and store sample specimens for subsequent analysis, including analysis with nucleic acid-based assays or immunoassays diagnostic for a particular pathogenic organism. When the sample specimen is a biological fluid, the sample specimen may be, for example, blood, urine, saliva, sputum, mucous or other bodily secretion, pus, amniotic fluid, cerebrospinal fluid or seminal fluid. However, the present invention also contemplates materials other than these specific biological fluids, including, but not limited to, water, chemicals and assay reagents, as well as solid substances which can be dissolved in whole or in part in a fluid milieu (e.g., tissue specimens, tissue culture cells, stool, environmental samples, food products, powders, particles and granules). Vessels used with the pierceable cap of the present invention are preferably capable of forming a substantially leak-proof seal with the pierceable cap and can be of any shape or composition, provided the vessel is shaped to receive and retain the material of interest (e.g., fluid specimen or assay reagents). Where the vessel contains a specimen to be assayed, it is important that the composition of the vessel be essentially inert so that it does not significantly interfere with the performance or results of an assay.

Embodiments of the present invention may lend themselves to sterile treatment of cell types contained in the vessel. In this manner, large numbers of cell cultures may be screened and maintained automatically. In situations where a cell culture is intended, a leak-proof seal is preferably of the type that permits gases to be exchanged across the membrane or seal. In other situations, where the vessels are pre-filled with transport media, stability of the media may be essential. The membrane or seal, therefore, may have very low permeability.

FIGS. 1A-1G show an embodiment of a pierceable cap 11. The pierceable cap 11 may include a shell 13, a frangible layer 15, and, optionally, a gasket 17.

The shell 13 may be generally cylindrical in shape or any other shape suitable for covering an opening 19 of a vessel 21. The shell 13 is preferably made of plastic resin, but may be made of any suitable material. The shell 13 may be molded by injection molding or other similar procedures. Based on the guidance provided herein, those skilled in the will be able to select a resin or mixture of resins having hardness and penetration characteristics which are suitable for a particular application, without having to engage in anything more than routine experimentation. Additionally, skilled artisans will realize that the range of acceptable cap resins will also depend on the nature of the resin or other material used to form the vessel 21, since the properties of the resins used to form these two components will affect how well the cap 11 and vessel 21 can form a leak proof seal and the ease with which the cap can be securely screwed onto the vessel. To modify the rigidity and penetrability of a cap, those skilled in the art will appreciate that the molded material may be treated, for example, by heating, irradiating or quenching. The shell 13 may have ridges or grooves to facilitate coupling of the cap 11 to a vessel 21.

The cap 11 may be injection molded as a unitary piece using procedures well known to those skilled in the art of injection molding, including a multi-gate process for facilitating uniform resin flow into the cap cavity used to form the shape of the cap.

The vessel 21 may be a test tube, but may be any other suitable container for holding a sample specimen.

The frangible layer 15 may be a layer of material located within an access port 23. For the purposes of the present invention, "frangible" means pierceable or tearable. Preferably, the access port 23 is an opening through the shell 13 from a top end 37 of the shell 13 to an opposite, bottom end 38 of the shell 13. If the shell 13 is roughly cylindrical, then the access port 23 may pass through the end of the roughly cylindrical shell 13. The access port 23 may also be roughly cylindrical and may be concentric with a roughly cylindrical shell 13.

Figure 2A:
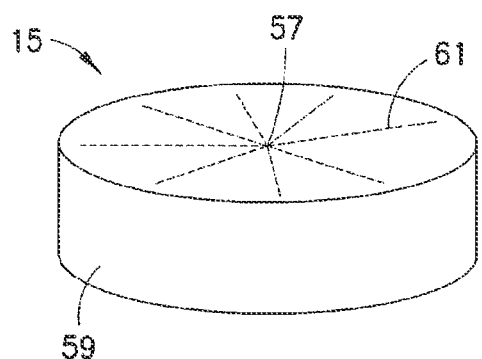
FIG. 2A is a perspective view of a possible frangible layer diaphragm.
Figure 2B:
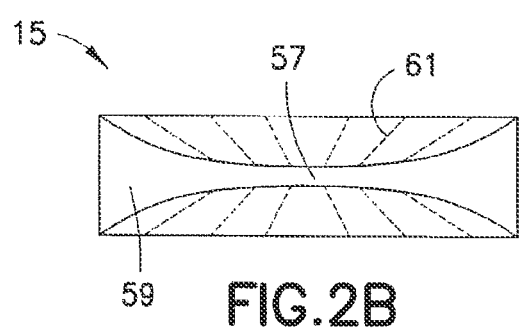
FIG. 2B is a cross-sectional view of the frangible layer of FIG. 2A.
Figure 3A:
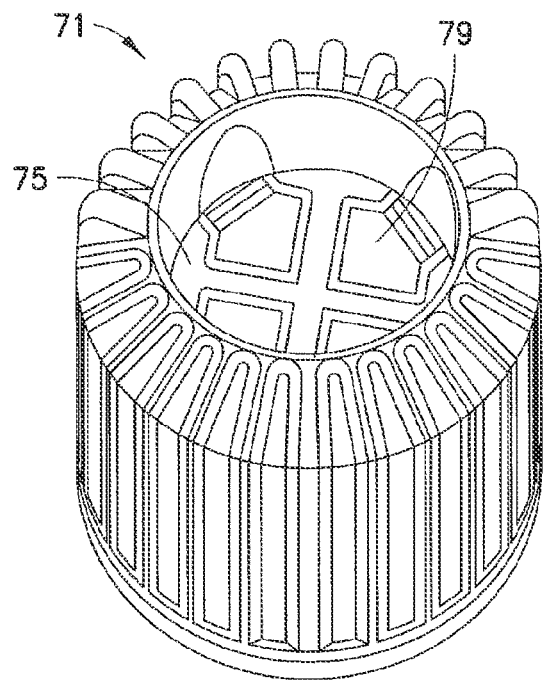
FIG. 3A is a perspective view of a pierceable cap with a foil frangible layer.
Figure 3B:
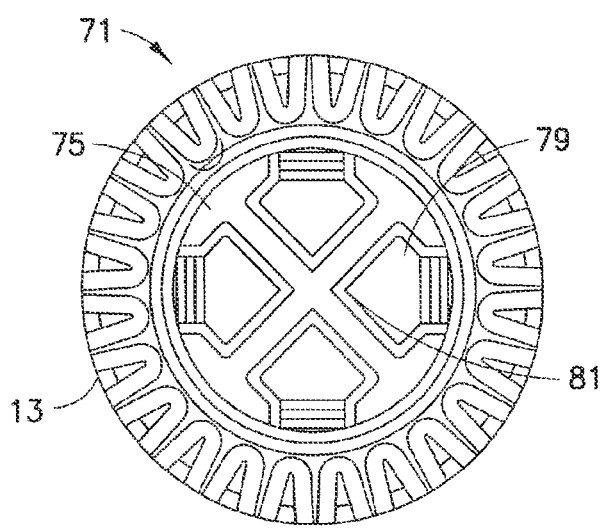
FIG. 3B is a top view of the pierceable cap of FIG. 3A.
Figure 3C:
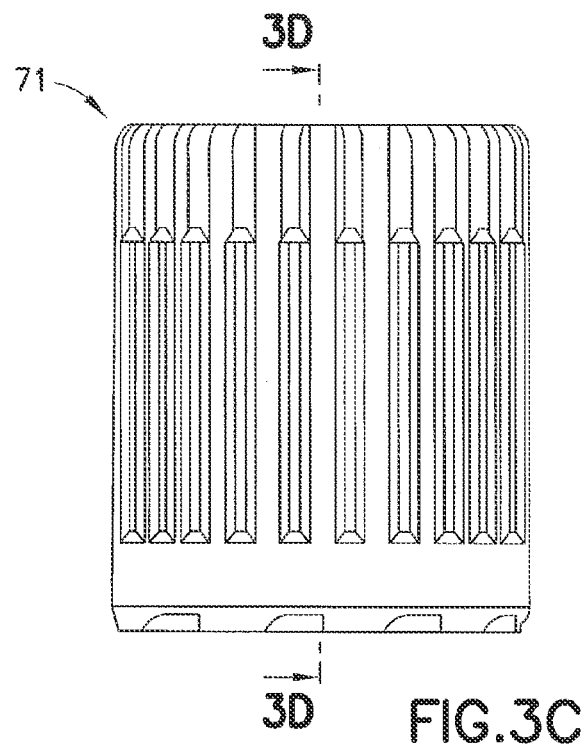
FIG. 3C is a side view of the pierceable cap of FIG. 3A.
Figure 3D:
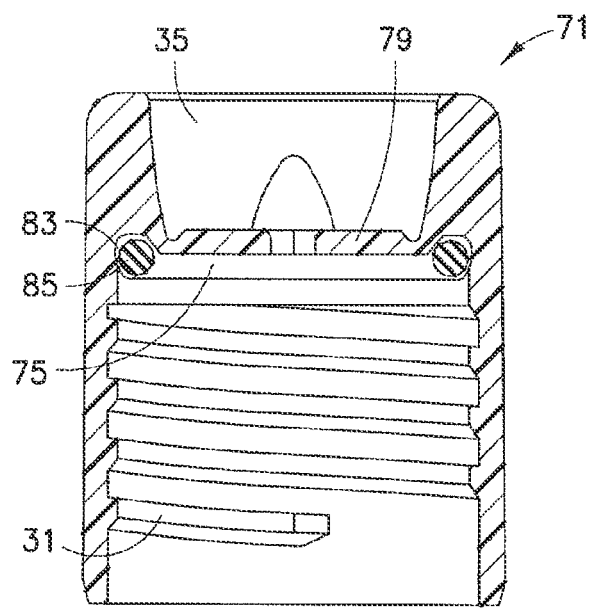
FIG. 3D is a cross-sectional view of the pierceable cap of FIG. 3C.
Figure 3E:
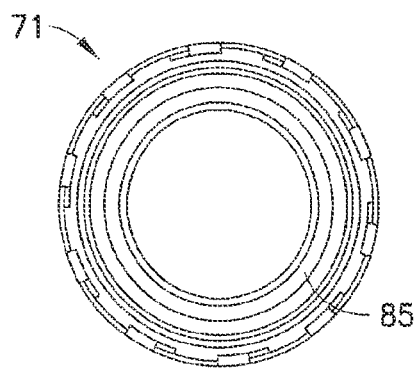
FIG. 3E is a bottom view as molded of the pierceable cap of FIG. 3A.
Figure 3F:
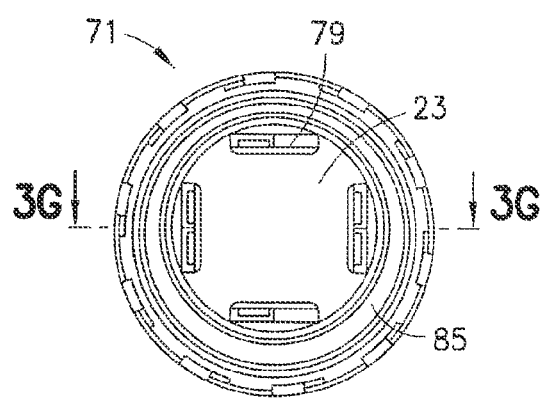
FIG. 3F is a bottom view of the pierceable cap of FIG. 3A pierced with foil not shown.
Figure 3G:
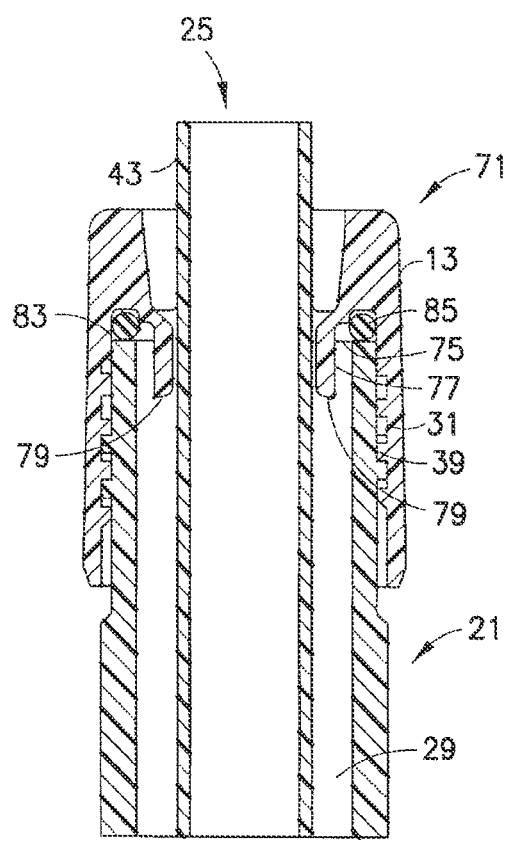
FIG. 3G is a cross-sectional view of the pierceable cap of FIG. 3A coupled to a vessel with a pipette tip inserted through the cap.

The frangible layer 15 may be disposed within the access port 23 such that transfer of the sample specimen through the access port is reduced or eliminated. In FIGS. 1A-1G, the frangible layer 15 is a diaphragm. Preferably, the frangible layer 15 is a thin, multilayer membrane with a consistent cross-section. Alternative frangible layers 15 are possible. For example, FIGS. 2A-2B, not shown to scale, are exemplary frangible layers 15 in the form of diaphragms. The frangible layer 15 is preferably made of rubber, but may be made of plastic, foil, combinations thereof or any other suitable material. The frangible layer may also be a Mylar or metal coated Mylar fused, resting, or partially resting upon an elastic diaphragm. A diaphragm may also serve to close the access port 23 after a transfer of the sample specimen to retard evaporation of any sample specimen remaining in the vessel 21. The frangible layer 15 may be thinner in a center 57 of the frangible layer 15 or in any position closest to where a break in the frangible layer 15 is desired. The frangible layer 15 may be thicker at a rim 59 where the frangible layer 15 contacts the shell 13 and/or the optional gasket 17. Alternatively, the frangible layer 15 may be thicker at a rim 59 such that the rim 59 of the frangible layer 15 forms a functional gasket within the shell 13 without the need for the gasket 17. The frangible layer 15 is preferably symmetrical radially and top to bottom such that the frangible layer 15 may be inserted into the cap 11 with either side facing a well 29 in the vessel 21. The frangible layer 15 may also serve to close the access port 23 after use of a transfer device 25. A peripheral groove 53 may be molded into the shell 13 to secure the frangible layer 15 in the cap 11 and/or to retain the frangible layer 15 in the cap 11 when the frangible layer 15 is pierced. The peripheral groove 53 in the cap 11 may prevent the frangible layer 15 from being pushed down into the vessel 21 by a transfer device 25. One or more pre-formed scores or slits 61 may be disposed in the frangible layer 15. The one or more preformed scores or slits 61 may facilitate breaching of the frangible layer 15. The one or more preformed scores or slits 61 may be arranged radially or otherwise for facilitating a breach of the frangible layer 15.

The frangible layer 15 may be breached during insertion of a transfer device 25. Breaching of the frangible layer 15 may include piercing, tearing open or otherwise destroying the structural integrity and seal of the frangible layer 15. The frangible layer 15 may be breached by a movement of one or more extensions 27 around or along a coupling region 47 toward the well 29 in the vessel 21. The frangible layer 15 may be disposed between the one or more extensions 27 and the vessel 21 when the one or more extensions 27 are in an initial position.

In certain embodiments, the frangible layer 15 and the one or more extensions 27 may be of a unitary construction. In some embodiments, the one or more extensions 27 may be positioned in a manner to direct or realign a transfer device 25 so that the transfer device 25 may enter the vessel 21 in a precise orientation. In this manner, the transfer device 25 may be directed to the center of the well 29, down the inner side of the vessel 21 or in any other desired orientation.

In embodiments of the present invention, the one or more extensions 27 may be generated by pre-scoring a pattern, for example, a "+" in the pierceable cap 11 material. In alternative embodiments, the one or more extensions 27 may be separated by gaps. Gaps may be of various shapes, sizes and configuration depending on the desired application. In certain embodiments, the pierceable cap 11 may be coated with a metal, such as gold, through a vacuum metal discharge apparatus or by paint. In this manner, a pierced cap may be easily visualized and differentiated from a non-pierced cap by the distortion in the coating.

The one or more extensions 27 may be integrally molded with the shell 13. The one or more extensions 27 may have different configurations depending on the use. The one or more extensions 27 may be connected to the shell 13 by the one or more coupling regions 47. The one or more extensions 27 may include points 49 facing into the center of the cap 11 or toward a desired breach point of the frangible layer 15. The one or more extensions 27 may be paired such that each leaf faces an opposing leaf. Preferred embodiments of the present invention may include four or six extensions arranged in opposing pairs. FIGS. 1A-1G show four extensions. The one or more coupling regions 47 are preferably living hinges, but may be any suitable hinge or attachment allowing the one or more extensions to move and puncture the frangible layer 15.

The access port 23 may be at least partially obstructed by the one or more extensions 27. The one or more extensions 27 may be thin and relatively flat. Alternatively, the one or more extensions 27 may be leaf-shaped. Other sizes, shapes and configurations are possible. The access port 23 may be aligned with the opening 19 of the vessel 21.

The gasket 17 may be an elastomeric ring between the frangible layer 15 and the opening 19 of the vessel 21 or the frangible layer 15 and the cap 11 for preventing leakage before the frangible layer 15 is broken. In some embodiments of the invention, the gasket 17 and the frangible layer 15 may be integrated as a single part.

A surface 33 may hold the frangible layer 15 against the gasket 17 and the vessel 21 when the cap 11 is coupled to the vessel 21. An exterior recess 35 at a top 37 of the cap 11 may be disposed to keep wet surfaces out of reach of a user's fingers during handling Surfaces of the access portal 23 may become wet with portions of the sample specimen during transfer. The exterior recess 35 may reduce or eliminate contamination by preventing contact by the user or automated capping/de-capping instruments with the sample specimen during a transfer. The exterior recess 35 may offset the frangible layer 15 away from the top end 37 of the cap 11 toward the bottom end 38 of the cap 11.

The shell 13 may include screw threads 31 or other coupling mechanisms for joining the cap 11 to the vessel 15. Coupling mechanisms preferably frictionally hold the cap 11 over the opening 19 of the vessel 21 without leaking. The shell 13 may hold the gasket 17 and the frangible layer 15 against the vessel 21 for sealing in the sample specimen without leaking. The vessel 21 preferably has complementary threads 39 for securing and screwing the cap 11 on onto the vessel. Other coupling mechanisms may include complementary grooves and/or ridges, a snap-type arrangement, or others.

The cap 11 may initially be separate from the vessel 21 or may be shipped as coupled pairs. If the cap 11 and the vessel 21 are shipped separately, then a sample specimen may be added to the vessel 21 and the cap 11 may be screwed onto the complementary threads 39 on the vessel 21 before transport. If the cap 11 and the vessel 21 are shipped together, the cap 11 may be removed from the vessel 11 before adding a sample specimen to the vessel 21. The cap 11 may then be screwed onto the complementary threads 39 on the vessel 21 before transport. At a testing site, the vessel 21 may be placed in an automated transfer instrument without removing the cap 11. Transfer devices 25 are preferably pipettes, but may be any other device for transferring a sample specimen to and from the vessel 21. When a transfer device tip 41 enters the access port 23, the transfer device tip 41 may push the one or more extensions 27 downward toward the well 29 of the vessel 21. The movement of the one or more extensions 27 and related points 49 may break the frangible layer 15. As a full shaft 43 of the transfer device 25 enters the vessel 21 through the access port 23, the one or more extensions 27 may be pushed outward to form airways or vents 45 between the frangible layer 15 and the shaft 43 of the transfer device 25. The airways or vents 45 may allow air displaced by the tip 41 of the transfer device to exit the vessel 21. The airways or vents 45 may prevent contamination and maintain pipetting accuracy. Airways or vents 45 may or may not be used for any embodiments of the present invention.

The action and thickness of the one or more extensions 27 may create airways or vents 45 large enough for air to exit the well 29 of the vessel 21 at a low velocity. The low velocity exiting air preferably does not expel aerosols or small drops of liquid from the vessel. The low velocity exiting air may reduce contamination of other vessels or surfaces on the pipetting instrument. In some instances, drops of the sample specimen may cling to an underside surface 51 of the cap 11. In existing systems, if the drops completely filled and blocked airways on a cap, the sample specimen could potentially form bubbles and burst or otherwise create aerosols and droplets that would be expelled from the vessel and cause contamination. In contrast, the airways and vents 45 created by the one or more extensions 27, may be large enough such that a sufficient quantity of liquid cannot accumulate and block the airways or vents 45. The large airways or vents 45 may prevent the pressurization of the vessel 21 and the creation and expulsion of aerosols or droplets. The airways or vents 45 may allow for more accurate transfer of the sample specimens.

An embodiment may include a molded plastic shell 13 to reduce costs. The shell 13 may be made of polypropylene for sample compatibility and for providing a resilient living hinge 47 for the one or more extensions 27. The cap 11 may preferably include three to six dart-shaped extensions 27 hinged at a perimeter of the access portal 23. For moldability, the portal may have a planar shut-off, 0.030" gaps between extensions 27, and a 10 degree draft. The access portal 23 may be roughly twice the diameter of the tip 41 of the transfer device 25. The diameter of the access portal 23 may be wide enough for adequate venting yet small enough that the one or more extensions 27 have space to descend into the vessel 21. The exterior recess 25 in the top of the shell 13 may be roughly half the diameter of the access portal 23 deep, which prevents any user's finger tips from touching the access portal.

FIGS. 3A-3G show an alternative embodiment of a cap 71 with a foil laminate used as a frangible layer 75. The frangible layer 75 may be heat welded or otherwise coupled to an underside 77 of one or more portal extensions 79. During insertion of a transfer device 25, the frangible layer 75 may be substantially ripped as the one or more portal extensions 79 are pushed toward the well 29 in the vessel or as tips 81 of the one or more portal extensions 79 are spread apart. The foil laminate of the frangible layer 75 may be inserted or formed into a peripheral groove 83 in the cap 71. An O-ring 85 may also be seated within the peripheral groove 83 for use as a sealing gasket. The peripheral groove 83 may retain the O-ring 85 over the opening 29 of the vessel 21 when the cap 71 is coupled to the vessel 21. The cap 71 operates similarly to the above caps.

Figure 4A:
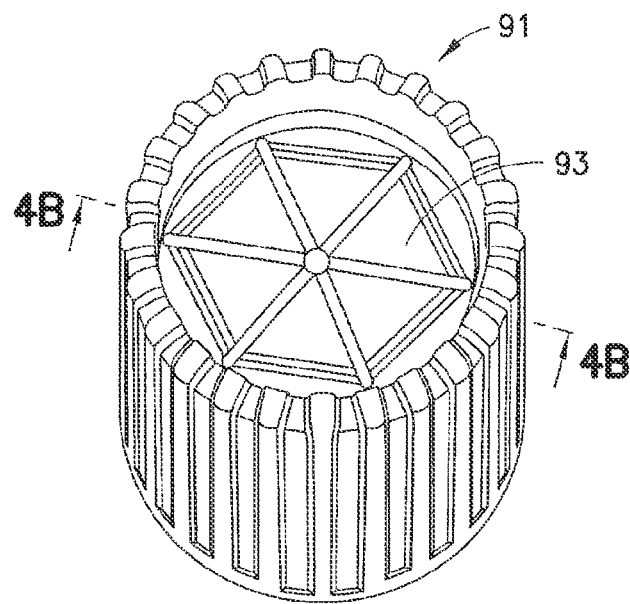
FIG. 4A is a perspective view of a pierceable cap with a lower frangible layer and extensions in a flat star pattern.
Figure 4B:
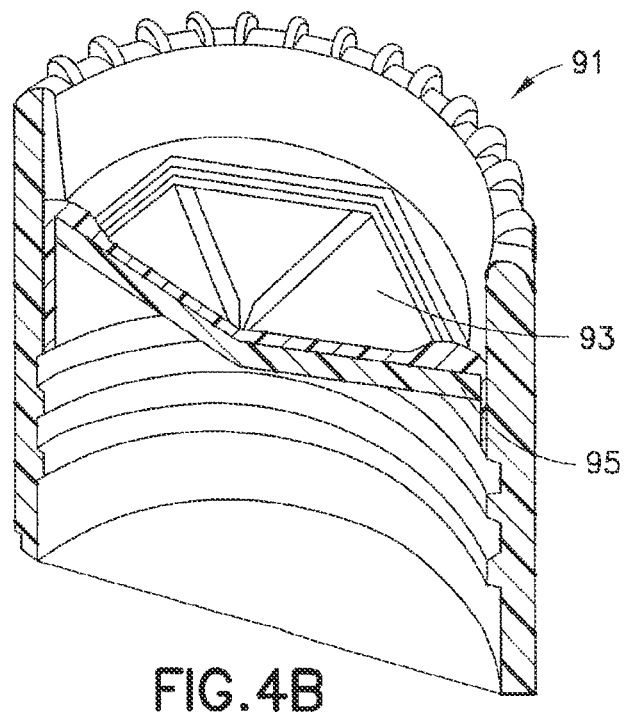
FIG. 4B is a perspective cut away view of the pierceable cap of FIG. 4A.

FIGS. 4A and 4B show an alternative cap 91 with an elastomeric sheet material as a frangible layer 95. The frangible layer 95 may be made of easy-tear silicone, such as a silicone sponge rubber with low tear strength, hydrophobic Teflon, or other similar materials. The frangible layer 95 may be secured adjacent to or adhered to the cap 91 for preventing unwanted movement of the frangible layer 95 during transfer of the sample specimen. The elastomeric material may function as a vessel gasket and as the frangible layer 95 in the area of a breach. One or more extensions 93 may breach the frangible layer 95. The cap 91 operates similarly to the above caps.

Figure 5A:
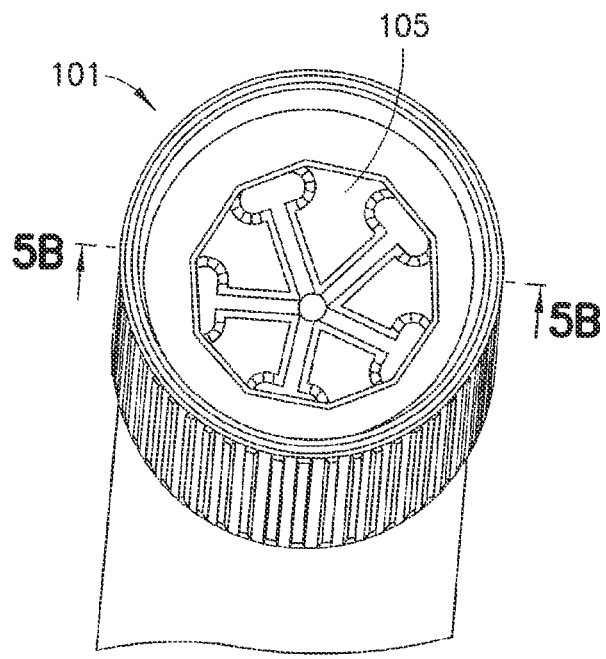
FIG. 5A is a perspective view of a pierceable cap with a conical molded frangible layer and extensions in a flat star pattern.
Figure 5B:
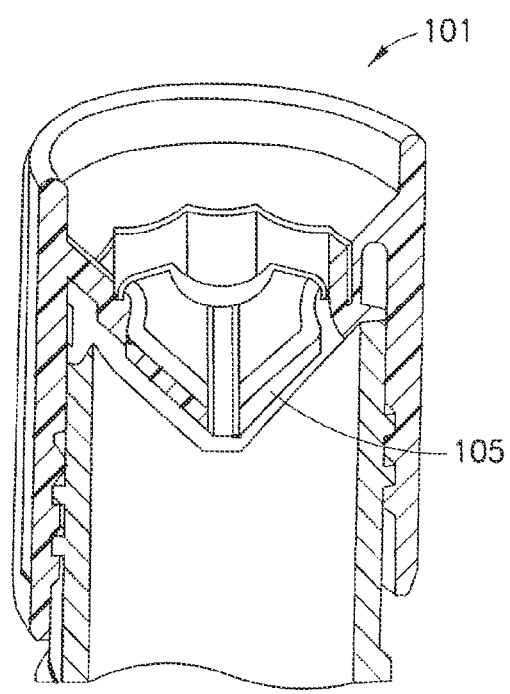
FIG. 5B is a cross section view of the pierceable cap of FIG. 5A.
Figure 6A:
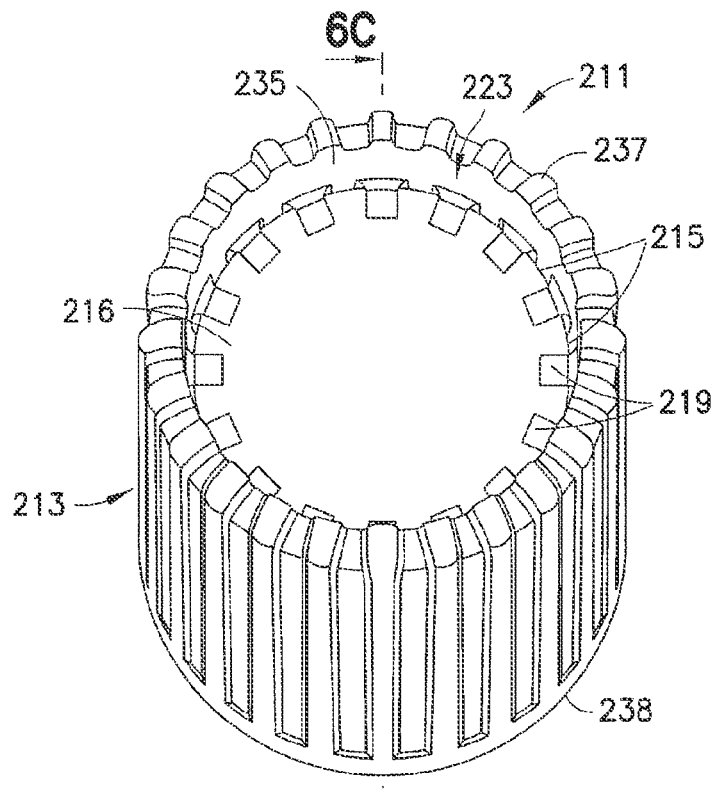
FIG. 6A is a perspective top view of a pierceable cap with two frangible layers with a moderately recessed upper frangible layer.
Figure 6B:
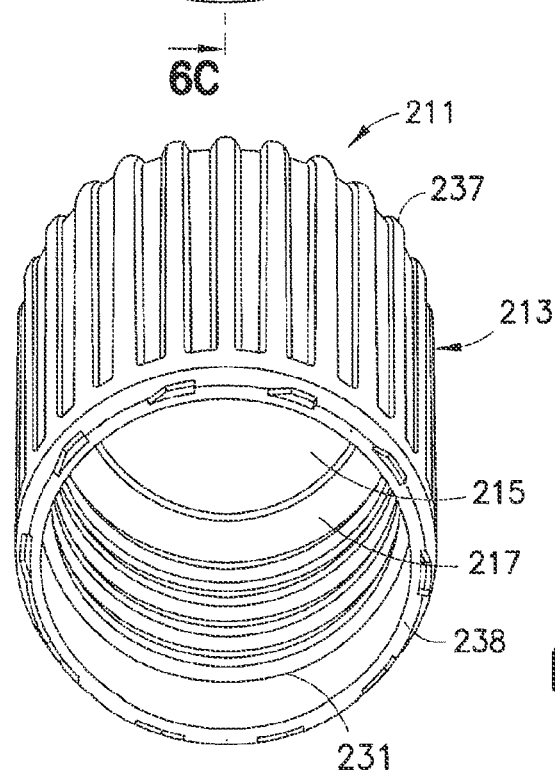
FIG. 6B is a perspective bottom view of the pierceable cap of FIG. 6A.
Figure 6C:
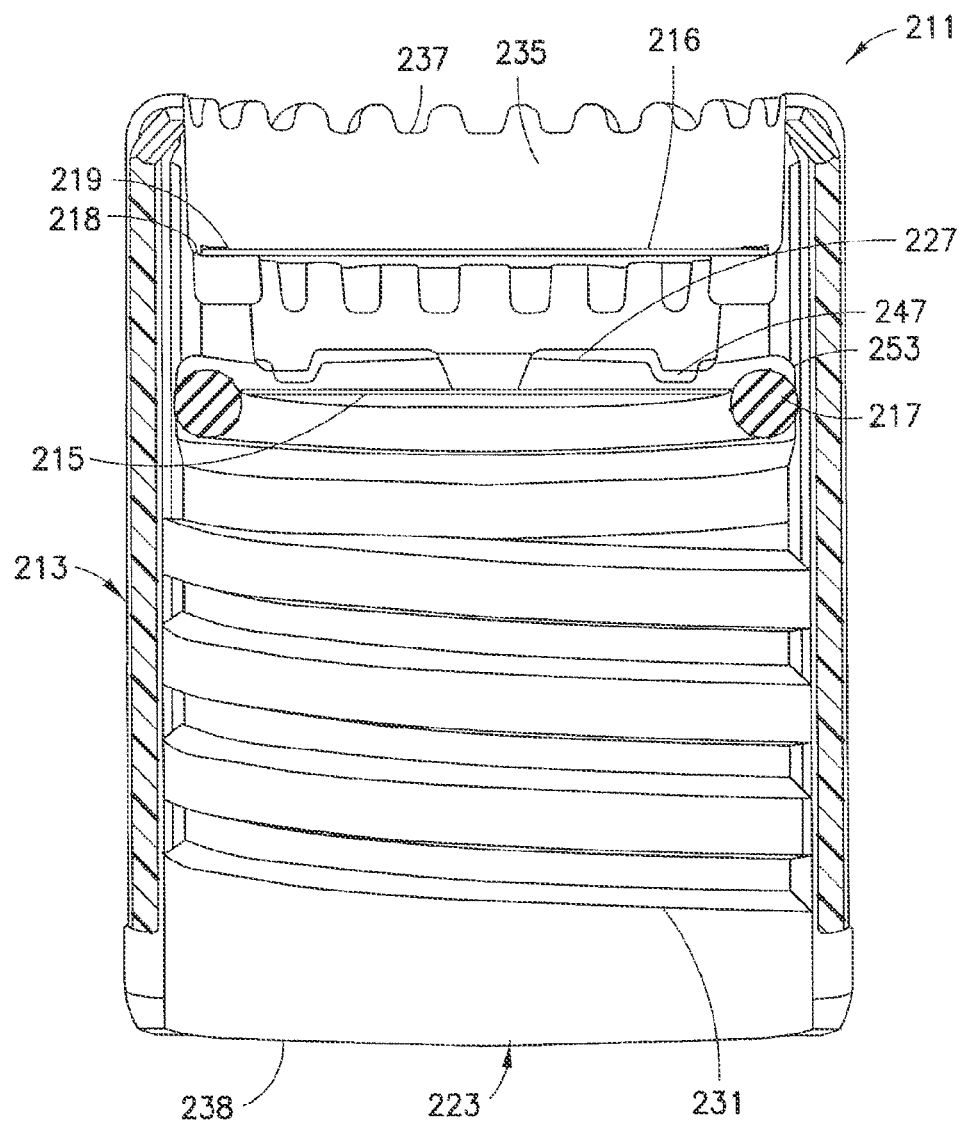
FIG. 6C is a cross-sectional view of the pierceable cap of FIG. 6A.
Figure 6D:
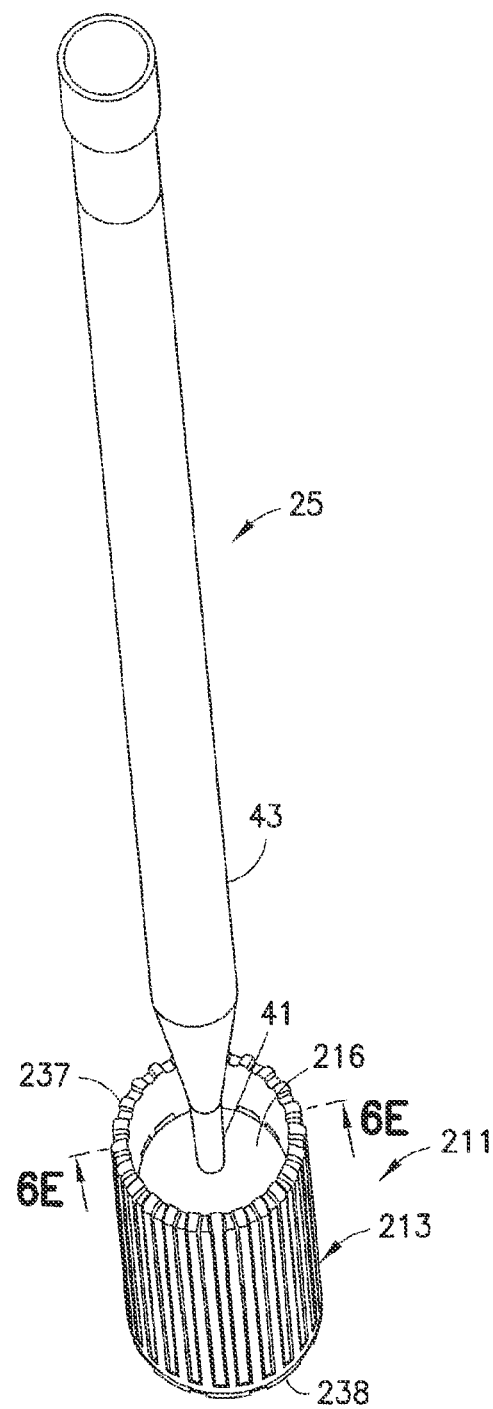
FIG. 6D is a perspective view of the pierceable cap of FIG. 6A with a pipette tip inserted through the two frangible layers.
Figure 6E:
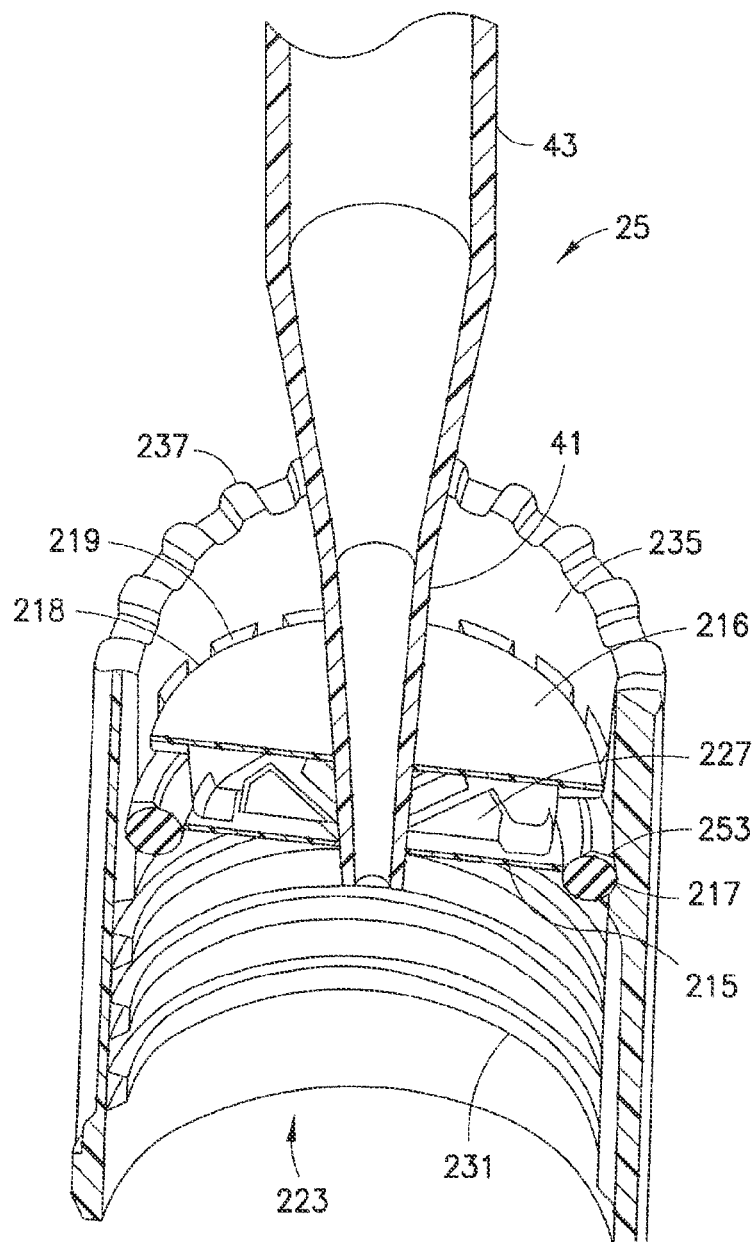
FIG. 6E is a cross-sectional view of the pierceable cap of FIG. 6A with a pipette tip inserted through the two frangible layers.

FIGS. 5A-5B show an alternative cap 101 with a conical molded frangible layer 105 covered by multiple extensions 107. The cap 101 operates similarly to the above caps.

FIGS. 6A-6E show an alternative cap 211 with multiple frangible layers 215, 216. The pierceable cap 211 may include a shell 213, a lower frangible layer 215, one or more upper frangible layers 216, and, optionally, a gasket 217. Where not specified, the operation and components of the alternative cap 211 are similar to those described above.

The shell 213 may be generally cylindrical in shape or any other shape suitable for covering an opening 19 of a vessel 21 as described above. The shell 213 of the alternative cap 211 may include provisions for securing two or more frangible layers. The following exemplary embodiment describes a pierceable cap 211 with a lower frangible layer 215 and an upper frangible layer 216, however, it is anticipated that more frangible layers may be used disposed in series above the lower frangible layer 215.

The frangible layers 215, 216 may be located within an access port 223. The lower frangible layer 215 is generally disposed as described above. Preferably, the access port 223 is an opening through the shell 213 from a top end 237 of the shell 213 to an opposite, bottom end 238 of the shell 213. If the shell 213 is roughly cylindrical, then the access port 223 may pass through the ends of the roughly cylindrical shell 213. The access port 223 may also be roughly cylindrical and may be concentric with a roughly cylindrical shell 213.

The frangible layers 215, 216 may be disposed within the access port 223 such that transfer of the sample specimen through the access port is reduced or eliminated. In FIGS. 6A-6E, the frangible layers 215, 216 may be foil. The foil may be any type of foil, but in preferred embodiments may be 100-micron, 38-micron, 20 micron, or any other size foil. More preferably, the foil for the upper frangible layer 216 is 38 micron or 20-micron size foil to prevent bending of tips 41 of the transfer devices 25. Exemplary types of foil that may be used in the present invention include "Easy Pierce Heat Sealing Foil" from ABGENE or "Thermo-Seal Heat Sealing Foil" from ABGENE. Other types of foils and frangible materials may be used. In preferred embodiments of the present invention, the foil may be a composite of several types of materials. The same or different selected materials may be used in the upper frangible layer 216 and the lower frangible layer 215. Furthermore, the upper frangible layer 216 and the lower frangible layer 225 may have the same or different diameters. The frangible layers 215, 216 may be bonded to the cap by a thermal process such as induction heating or heat sealing.

A peripheral groove 253 may be molded into the shell 213 to secure the lower frangible layer 215 in the pierceable cap 211 and/or to retain the lower frangible layer 215 in the cap 211 when the lower frangible layer 215 is pierced. The peripheral groove 253 in the cap 211 may prevent the lower frangible layer 215 from being pushed down into the vessel 21 by a transfer device 25. One or more pre-formed scores or slits may be disposed in the lower frangible layer 215 or the upper frangible layer 216.

The one or more upper frangible layers 216 may be disposed within the shell 213 such that one or more extensions 227 are located between the lower frangible layer 215 and the upper frangible layer 216. Preferably, the distance between the lower frangible layer 215 and the upper frangible layer 216 is as large as possible. The distance may vary depending on several factors including the size of the transfer device. In some embodiments, the distance between the lower frangible layer 215 and the upper frangible layer 216 is approximately 0.2 inches. More preferably, the distance between the lower frangible layer 215 and the upper frangible layer is approximately 0.085 inches. In a preferred embodiment of the present invention, the gap may be 0.085 inches. The upper frangible layer 216 is preferably recessed within the access port 223 to prevent contamination by contact with a user's hand. Recessing the upper frangible layer 216 may further minimize manual transfer of contamination. The upper frangible layer 216 may block any jetted liquid upon puncture of the lower frangible layer 215.

The upper frangible layer 216 may sit flush with the walls of the access port 223 or may be vented with one or more vents 218. The one or more vents 218 may be created by spacers 219. The one or more vents 218 may diffuse jetted air during puncture and create a labyrinth for trapping any jetted air during puncture.

The upper frangible layer 216 preferably contacts the conical tip 41 of a transfer device 25 during puncture of the lower frangible layer 215. The upper frangible layer 216 may be breached before the breaching of the lower frangible layer 215. The frangible layers 215, 216 may be breached during insertion of a transfer device 25 into the access port 223. Breaching of the frangible layers 215, 216 may include piercing, tearing open or otherwise destroying the structural integrity and seal of the frangible layers 215, 216. The lower frangible layer 215 may be breached by a movement of one or more extensions 227 around or along a coupling region 247 toward a well 29 in the vessel 21. The lower frangible layer 215 may be disposed between the one or more extensions 227 and the vessel 21 when the one or more extensions 227 are in an initial position.

A gasket 217 may be an elastomeric ring between the lower frangible layer 215 and the opening 19 of the vessel 21 for preventing leakage before the frangible layers 215, 216 are broken.

An exterior recess 235 at a top 237 of the pierceable cap 211 may be disposed to keep wet surfaces out of reach of a user's fingers during handling Surfaces of the access portal 223 may become wet with portions of the sample specimen during transfer. The exterior recess 235 may reduce or eliminate contamination by preventing contact by the user or automated capping/de-capping instruments with the sample specimen during a transfer. The exterior recess 235 may offset the frangible layers 215, 216 away from the top end 237 of the cap 211 toward the bottom end 238 of the cap 211. The cap 211 may initially be separate from the vessel 21, until the sample is added thereto or may be combined with the vessel prior to the addition of samples. It is contemplated herein that the cap 211 may be shipped as coupled pairs. If the cap 211 and the vessel 21 are shipped separately, the sample specimen may be added to the vessel 21 and the cap 211 subsequently fastened onto the complementary threads on the vessel 21 before further transport and handling If the cap 211 and the vessel 21 are fastened and shipped together for shipment, the cap 211 may be removed from the vessel 21 before adding a sample specimen to the vessel 21. The cap 211 may then be refastened to the complementary threads on the vessel 21 before further transport and handling At a testing site, the vessel 21 may be placed in an automated fluid transfer instrument for sample removal without removing the cap 211.

The shell 213 may include screw threads 231 or other coupling mechanisms for joining the cap 211 to the vessel 15 as described above.

Transfer devices 25 are preferably pipettes, but may be any other device for transferring a sample specimen to and from the vessel 21. When a transfer device tip 41 enters the access port 223, the transfer device 41 may breach the upper frangible layer. The tip 41 of the transfer device may be generally conical while a shaft 43 may be generally cylindrical. As the conical tip 41 of the transfer device continues to push through the breached upper frangible layer 216, the opening of the upper frangible layer 216 may expand with the increasing diameter of the conical tip 41.

The tip 41 of the transfer device 25 may then contact and push the one or more extensions 227 downward toward the well 29 of the vessel 21. The movement of the one or more extensions 227 and related points may break the lower frangible layer 215. At this time, the conical tip 41 of the transfer device may still be in contact with the upper frangible layer 216. As the increasing diameter of the conical tip 41 and the full shaft 43 of the transfer device 25 enters the vessel 21 through the access port 223, the one or more extensions 227 may be pushed outward to form airways or vents between the lower frangible layer 215 and the shaft 43 of the transfer device 25. The created airways or vents may allow air displaced by the tip 41 of the transfer device 25 to exit the vessel 21. The airways or vents may prevent contamination and maintain pipetting accuracy. The upper frangible layer 216 prevents contamination by creating a seal with the transfer device tip 41 above the one or more extensions 227. Exiting air is vented 215 through a labyrinth-type path from the vessel to the external environment.

The upper frangible layer 216 in the pierceable cap 211 may have a different functionality than the lower frangible layer 215. The lower frangible layer 215, which may be bonded to the one or more extensions 227, may tear in a manner such that a relatively large opening is opened in the lower frangible layer 215. The relatively large opening may create a relatively large vent in the lower frangible layer 215 to eliminate or reduce pressurization from the insertion of the tip 41 of a transfer device 25. In contrast to the lower frangible layer 215, the upper frangible layer 216 may act as a barrier to prevent any liquid that may escape from the pierceable cap 211 after puncture of the lower frangible layer 215. The upper frangible layer 216 may be vented 215 at its perimeter to prevent pressurization of the intermediate volume between the upper frangible layer 216 and the lower frangible layer 215. The upper frangible layer 216 may also be vented 218 at its perimeter to diffuse any jetting liquid by creating multiple pathways for vented liquid and/or air to escape from the intermediate volume between the upper frangible layer 216 and the lower frangible layer 215.

The upper frangible layer 216 may be active on puncture, and may be located within the aperture of the pierceable cap 211 at a height such that the upper frangible layer 216 acts upon the conical tip 41 of the transfer device 25 when the lower frangible layer 215 is punctured. Acting on the conical tip 41 and not the cylindrical shaft 43 of the transfer device 25 may assure relatively close contact between the tip 41 and the upper frangible layer 216 and may maximize effectiveness of the upper frangible layer 216 as a barrier.

The selected material for the upper frangible layer 216 may tear open in a polygonal shape, typically hexagonal. When the conical tip 41 is fully engaged with the upper frangible layer 216 sufficient venting exists such that there is little or no impact on transfer volumes aspirated from or pipetted into the shaft 43 of the transfer device 25.

Alternatively, to the pierceable cap 211 depicted in FIGS. 6A-6E, the upper frangible layer 216 may be flush with a top 237 of the shell 213. Venting may or may not be used when the upper frangible layer 216 is flush with the top 237 of the shell 213. Preferably, the distance between the lower frangible layer 215 and the upper frangible layer is approximately 0.2 inches. The foil used with the upper frangible layer 216 flush with the top 237 of the shell may be a heavier or lighter foil or other material than that used with the lower frangible layer 215. Venting may or may not be used with any embodiments of the present invention.

Figure 7A:
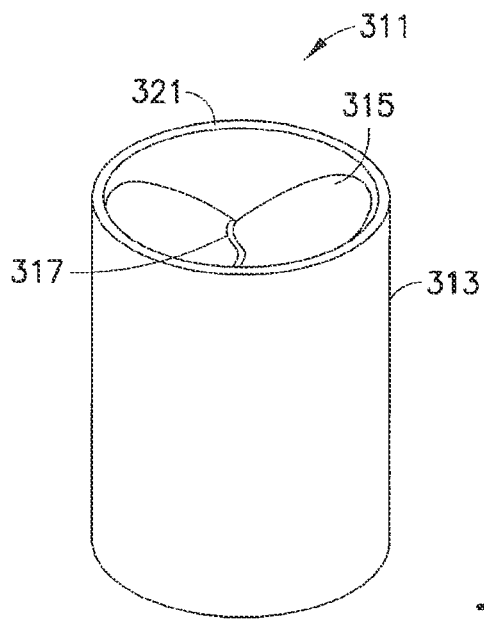
FIG. 7A is a perspective view of a pierceable cap with a V-shaped frangible layer.
Figure 7B:
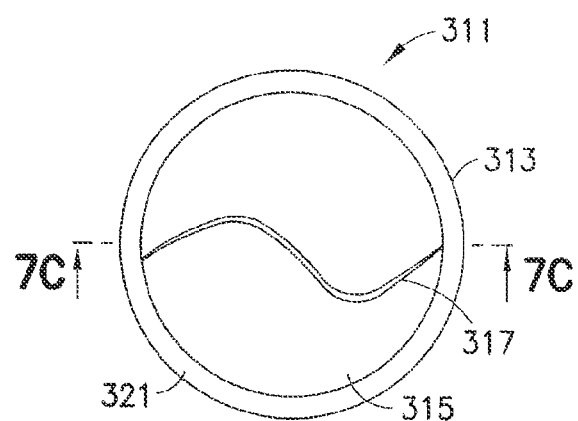
FIG. 7B is a top view of the pierceable cap of FIG. 7A.
Figure 7C:
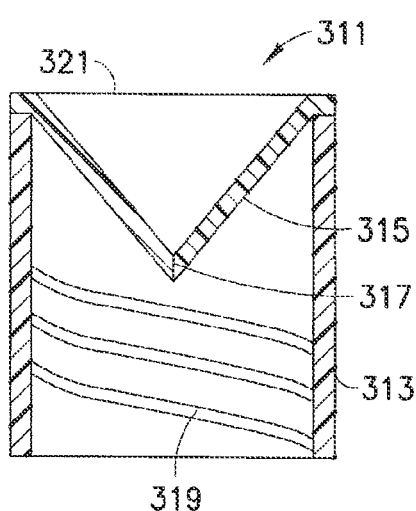
FIG. 7C is a cross-sectional view of the pierceable cap of FIG. 7B.
Figure 8A:
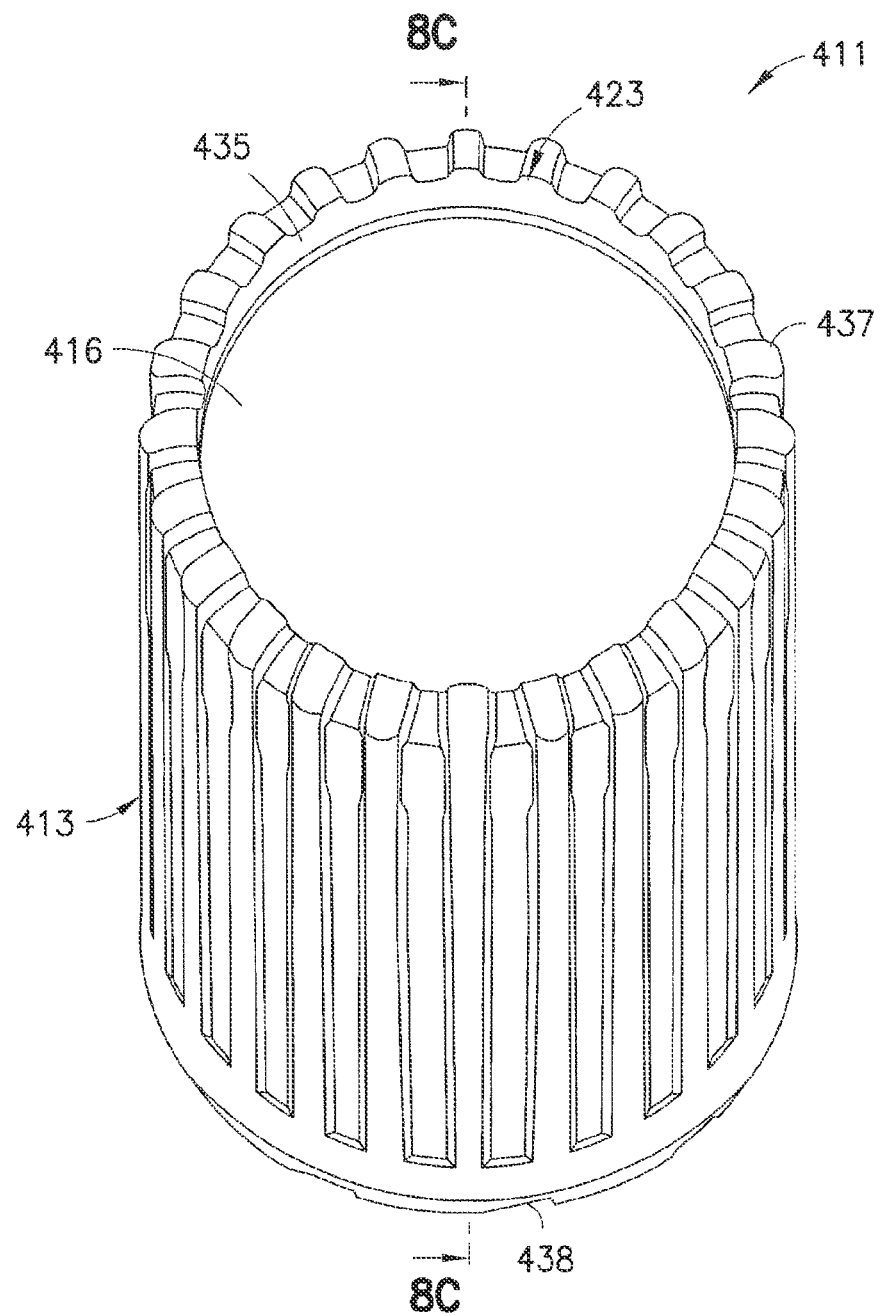
FIG. 8A is a perspective top view of a pierceable cap with two frangible layers with a slightly recessed upper frangible layer.
Figure 8B:
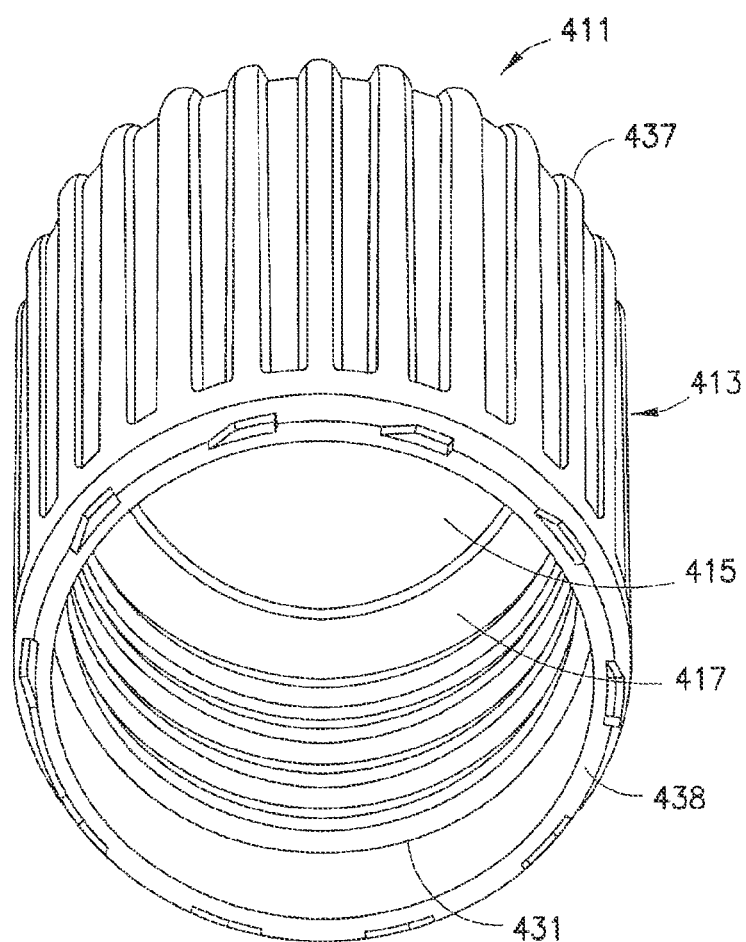
FIG. 8B is a perspective bottom view of the pierceable cap of FIG. 8A.
Figure 8C:
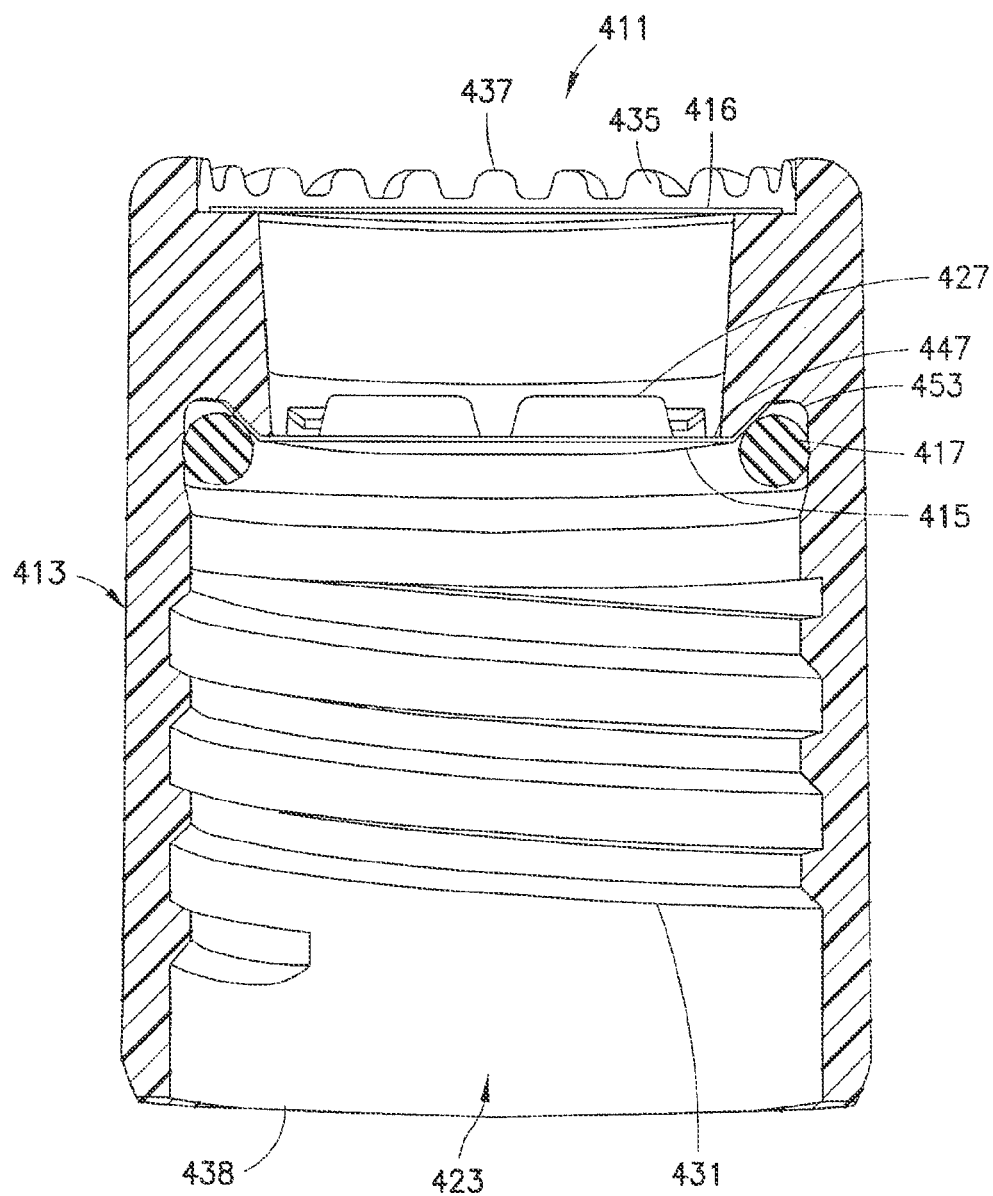
FIG. 8C is a cross-sectional view of the pierceable cap of FIG. 8A.
Figure 8D:
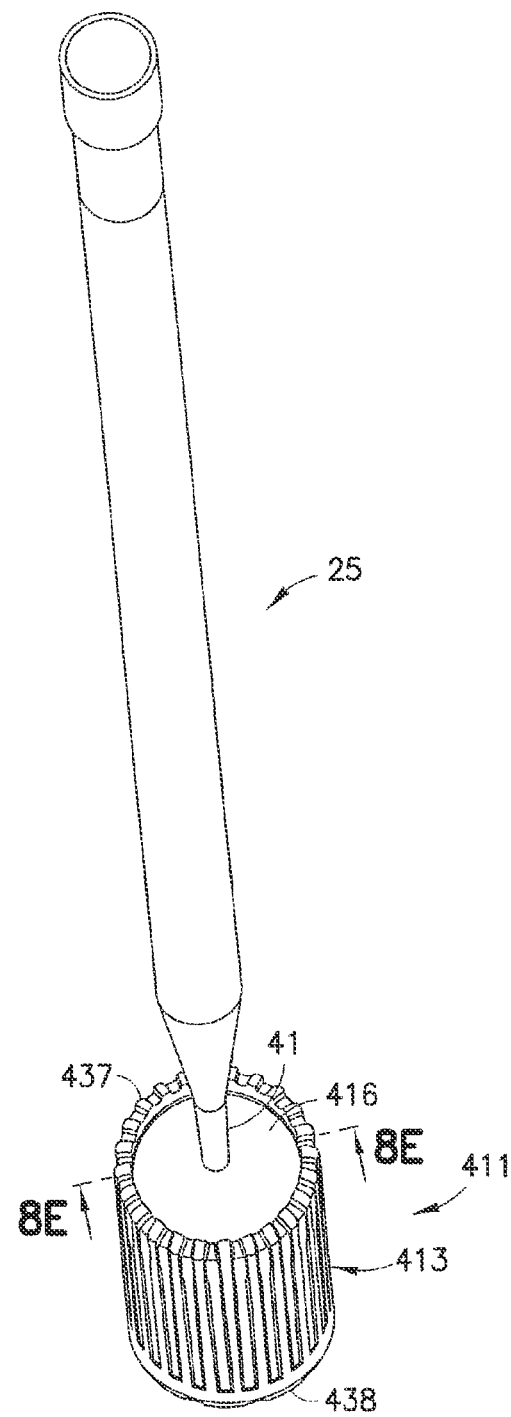
FIG. 8D is a perspective view of the pierceable cap of FIG. 8A with a pipette tip inserted through the two frangible layers.
Figure 8E:
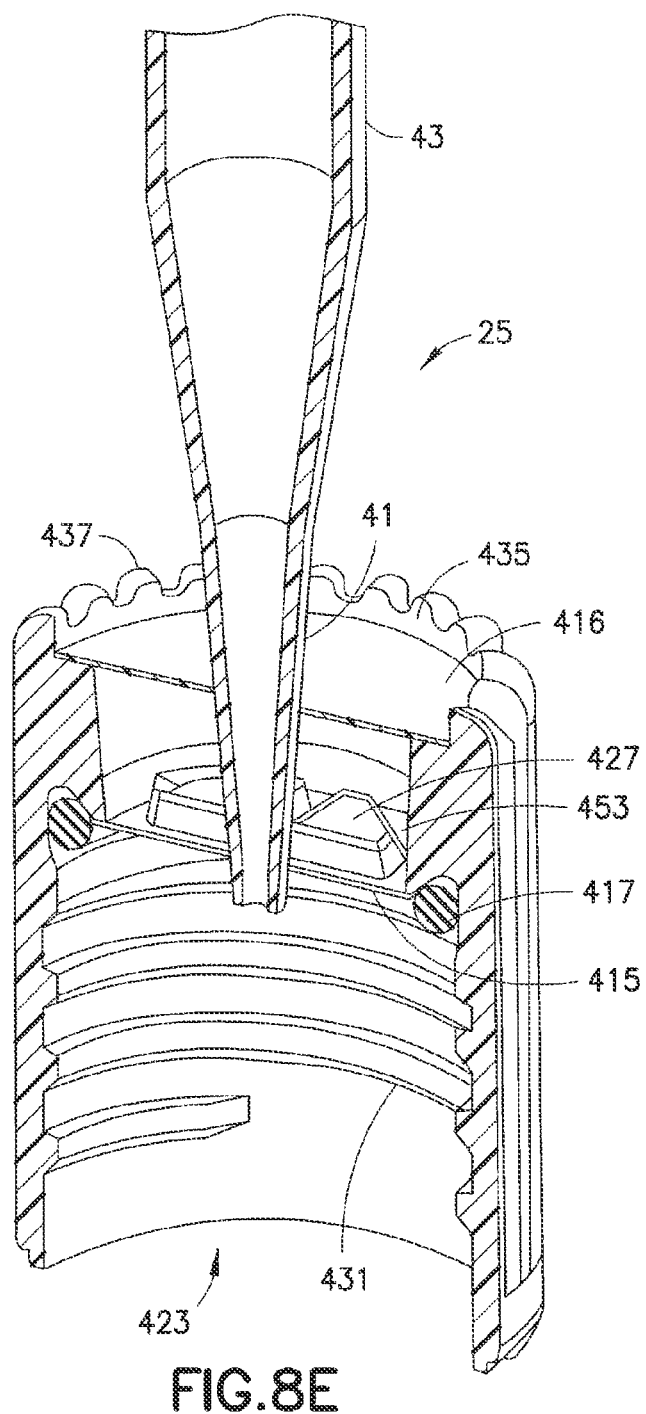
FIG. 8E is a cross-sectional view of the pierceable cap of FIG. 8D with a pipette tip inserted through the two frangible layers.

FIGS. 7A-7C show an alternative pierceable cap 311 with a V-shaped frangible layer 315 with a seal 317. The frangible layer 315 may be weakened in various patterns along a seal 317. In preferred embodiments of the present invention the seal 317 is sinusoidal in shape. The seal 317 may be linear or other shapes depending on particular uses. A sinusoidal shape seal 317 may improve sealing around a tip 41 of a transfer device 25 or may improve resealing qualities of the seal after removal of the transfer device 25 from the V-shaped frangible layer 315. Any partial resealing of the seal 317 may prevent contamination or improve storage of the contents of a vessel 21. Furthermore, a sinusoidal shape seal 317 may allow venting of the air within the vessel 21 during transfer of the contents of the vessel 21 with a transfer device 25. The frangible layer 315 may be weakened by scoring or perforating the frangible layer 315 to ease insertion of the transfer device 25. Alternatively, the frangible layer 315 may be constructed such that the seal 317 is thinner than the surrounding material in the frangible layer 315.

The pierceable cap 311 may include a shell 313, threads 319, and other components similar to those embodiments described above. Where not specified, the operation and components of the alternative cap 311 can include embodiments similar to those described above. In other alternate embodiments, described below, the pierceable cap is of unitary elastomeric construction. The skilled person will appreciate that the elastomeric seals described herein also can be adapted to be incorporated into the shell and seal embodiments described herein.

One or more additional frangible layers may be added to the pierceable cap 311 to further prevent contamination. For example, one or more additional frangible layers may be disposed closer to a top 321 of the shell 313 within an exterior recess (not shown). The V-shaped frangible seal 315 may be recessed within the shell 313 such that an upper frangible seal is added above the V-shaped frangible seal 315. Alternatively, an additional frangible layer may be flush with the top 321 of the shell 313. The operation and benefits of the upper frangible seal are discussed above.

FIGS. 8A-8E show an alternative cap 411 with multiple frangible layers 415, 416. The pierceable cap 411 may include a shell 413, a lower frangible layer 415, one or more upper frangible layers 416, and, optionally, a gasket 417. Where not specified, the operation and components of the alternative cap 411 are similar to those described above.

The shell 413 may be generally cylindrical in shape or any other shape suitable for covering an opening 19 of a vessel 21 as described above. The shell 413 of the alternative cap 411 may include provisions for securing two or more frangible layers. The following exemplary embodiment describes a pierceable cap 411 with a lower frangible layer 415 and an upper frangible layer 416, however, it is anticipated that more frangible layers may be used disposed in series above the lower frangible layer 415.

The frangible layers 415, 416 may be located within an access port 423. The lower frangible layer 415 is generally disposed as described above. Preferably, the access port 423 is an opening through the shell 413 from a top end 437 of the shell 413 to an opposite, bottom end 438 of the shell 413. If the shell 413 is roughly cylindrical, then the access port 423 may pass through the ends of the roughly cylindrical shell 413. The access port 423 may also be roughly cylindrical and may be concentric with a roughly cylindrical shell 413.

The frangible layers 415, 416 may be disposed within the access port 423 such that transfer of the sample specimen through the access port is reduced or eliminated. The frangible layers 415, 416 may be similar to those described above. In preferred embodiments of the present invention, the foil may be a composite of several types of materials. The same or different selected materials may be used in the upper frangible layer 416 and the lower frangible layer 415. Furthermore, the upper frangible layer 416 and the lower frangible layer 425 may have the same or different diameters. The frangible layers 415, 416 may be bonded to the cap by a thermal process such as induction heating or heat sealing.

A peripheral groove 453 may be molded into the shell 413 to secure the lower frangible layer 415 in the pierceable cap 411 and/or to retain the lower frangible layer 415 in the cap 411 when the lower frangible layer 415 is pierced. The peripheral groove 453 in the cap 411 may prevent the lower frangible layer 415 from being pushed down into the vessel 21 by a transfer device 25. One or more pre-formed scores or slits may be disposed in the lower frangible layer 415 or the upper frangible layer 416.

The one or more upper frangible layers 416 may be disposed within the shell 413 such that one or more extensions 427 are located between the lower frangible layer 415 and the upper frangible layer 416. Preferably, the distance between the lower frangible layer 415 and the upper frangible layer 416 is as large as possible. The distance may vary depending on several factors including the size of the transfer device. Preferably, the upper frangible layer 416 is only slightly recessed from the top end 437. The upper frangible layer 416 may block any jetted liquid upon puncture of the lower frangible layer 415. Preferably, no venting is associated with the upper frangible layer 416, however, venting could be used depending on particular applications.

The upper frangible layer 416 preferably contacts the conical tip 41 of a transfer device 25 during puncture of the lower frangible layer 415. The upper frangible layer 416 may be breached before the breaching of the lower frangible layer 415. The frangible layers 415, 416 may be breached during insertion of a transfer device 25 into the access port 423. Breaching of the frangible layers 415, 416 may include piercing, tearing open or otherwise destroying the structural integrity and seal of the frangible layers 415, 416. The lower frangible layer 415 may be breached by a movement of one or more extensions 427 around or along a coupling region 447 toward a well 29 in the vessel 21. The lower frangible layer 415 may be disposed between the one or more extensions 427 and the vessel 21 when the one or more extensions 427 are in an initial position.

A gasket 417 may be an elastomeric ring between the lower frangible layer 415 and the opening 19 of the vessel 21 for preventing leakage before the frangible layers 415, 416 are broken.

An exterior recess 435 at a top 437 of the pierceable cap 411 may be disposed to keep wet surfaces out of reach of a user's fingers during handling Surfaces of the access portal 423 may become wet with portions of the sample specimen during transfer. The exterior recess 435 may reduce or eliminate contamination by preventing contact by the user or automated capping/de-capping instruments with the sample specimen during a transfer. The exterior recess 435 may offset the frangible layers 415, 416 away from the top end 437 of the cap 411 toward the bottom end 438 of the cap 411.

The shell 413 may include screw threads 431 or other coupling mechanisms for joining the cap 411 to the vessel 15 as described above. The operation of the pierceable cap 411 is similar to those embodiments described above.

Embodiments of the present invention can utilize relatively stiff extensions in combination with relatively fragile frangible layers. Either the frangible layer and/or the stiff extensions can be scored or cut; however, embodiments where neither is scored or cut are also contemplated. Frangible materials by themselves may not normally open any wider than a diameter of the one or more piercing elements. In many situations, the frangible material may remain closely in contact with a shaft of a transfer device. This arrangement may provide inadequate venting for displaced air. Without adequate airways or vents a transferred volume may be inaccurate and bubbling and spitting of the tube contents may occur. Stiff components used alone to seal against leakage can be hard to pierce, even where stress lines and thin wall sections are employed to aid piercing. This problem can often be overcome, but requires additional costs in terms of quality control. Stiff components may be cut or scored to promote piercing, but the cutting and scoring may cause leakage. Materials that are hard to pierce may result in bent tips on transfer devices and/or no transfer at all. Combining a frangible component with a stiff yet moveable component may provide both a readily breakable seal and adequate airways or vents to allow accurate transfer of a sample specimen without contamination. In addition, in some embodiments, scoring of the frangible layer will not align with the scoring of the still components. This can most easily be forced by providing a frangible layer and stiff components that are self-aligning.

Furthermore, changing the motion profile of the tip of the transfer device during penetration may reduce the likelihood of contamination. Possible changes in the motion profile include a slow pierce speed to reduce the speed of venting air. Alternative changes may include aspirating with the pipettor or similar device during the initial pierce to draw liquid into the tip of the transfer device.

Figure 9:
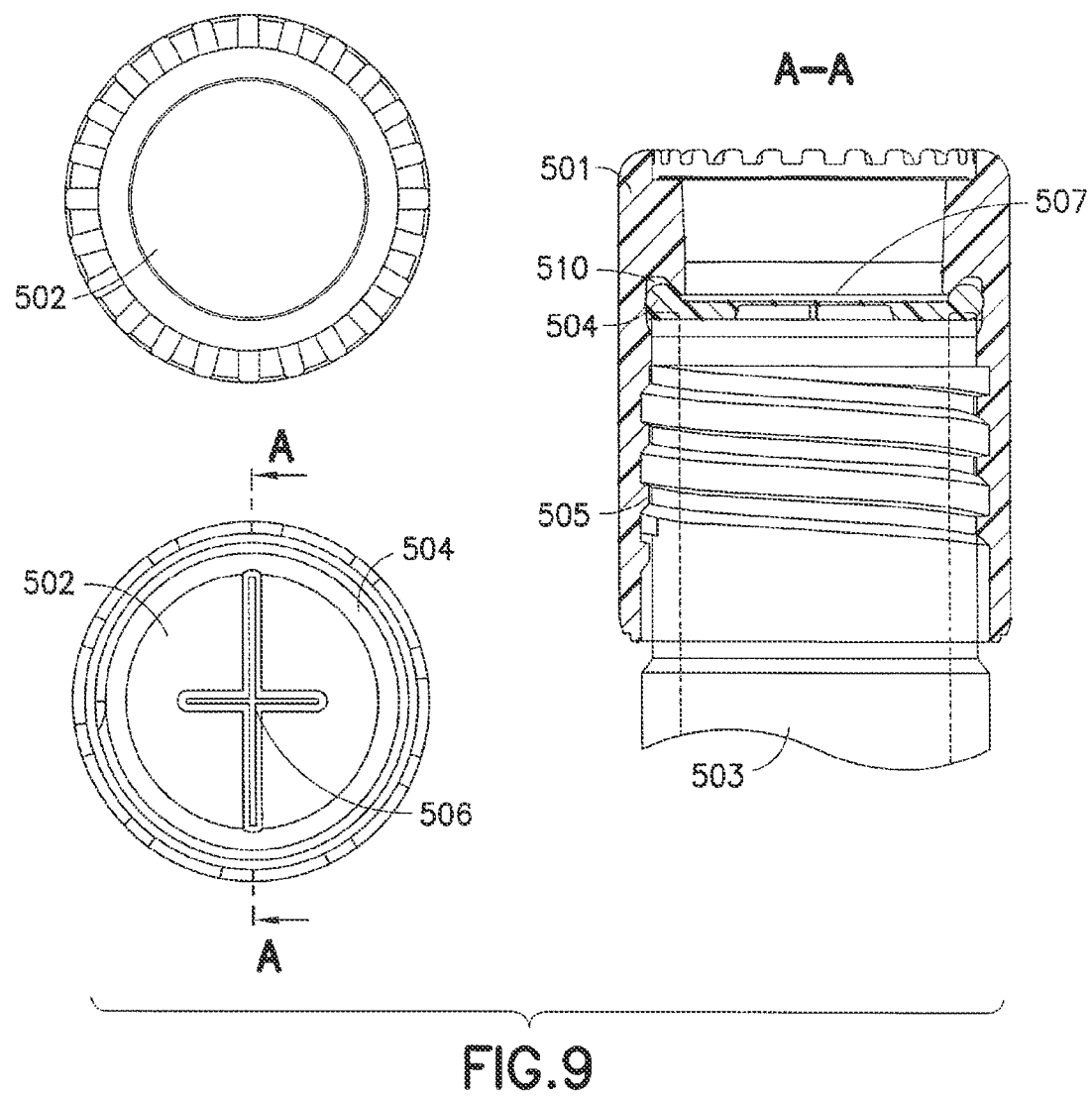
FIG. 9 is a top view and cross-sectional view of a single piece pierceable cap, having a pierceable, thin webbing.

FIG. 9 depicts another embodiment of a pierceable cap having a single frangible, membrane 502. The membrane 502 has elastomeric properties and contains a thin webbing 507, which provides a seal until it is pierced or otherwise breached by a transfer device. The webbing feature provides a structurally weakened membrane portion that controls how the seal splits, thus insuring proper function of the cap. This weakened membrane portion is achieved by making the membrane thinner in the portions designated for tearing. Alternatively, the membrane may be weakened by any other means known, such as perforations or scoring.

FIG. 9 depicts the pierceable cap shell 501, the frangible membrane 502 and the vessel (tube) 503. The O-ring feature 504 on the frangible membrane 502 is sealed to the tube by screwing the cap shell 501 along the threads 505. The elastomeric membrane 502 has a cross slit 506 that is closed by a very thin web of elastomeric material 507.

Figure 10:
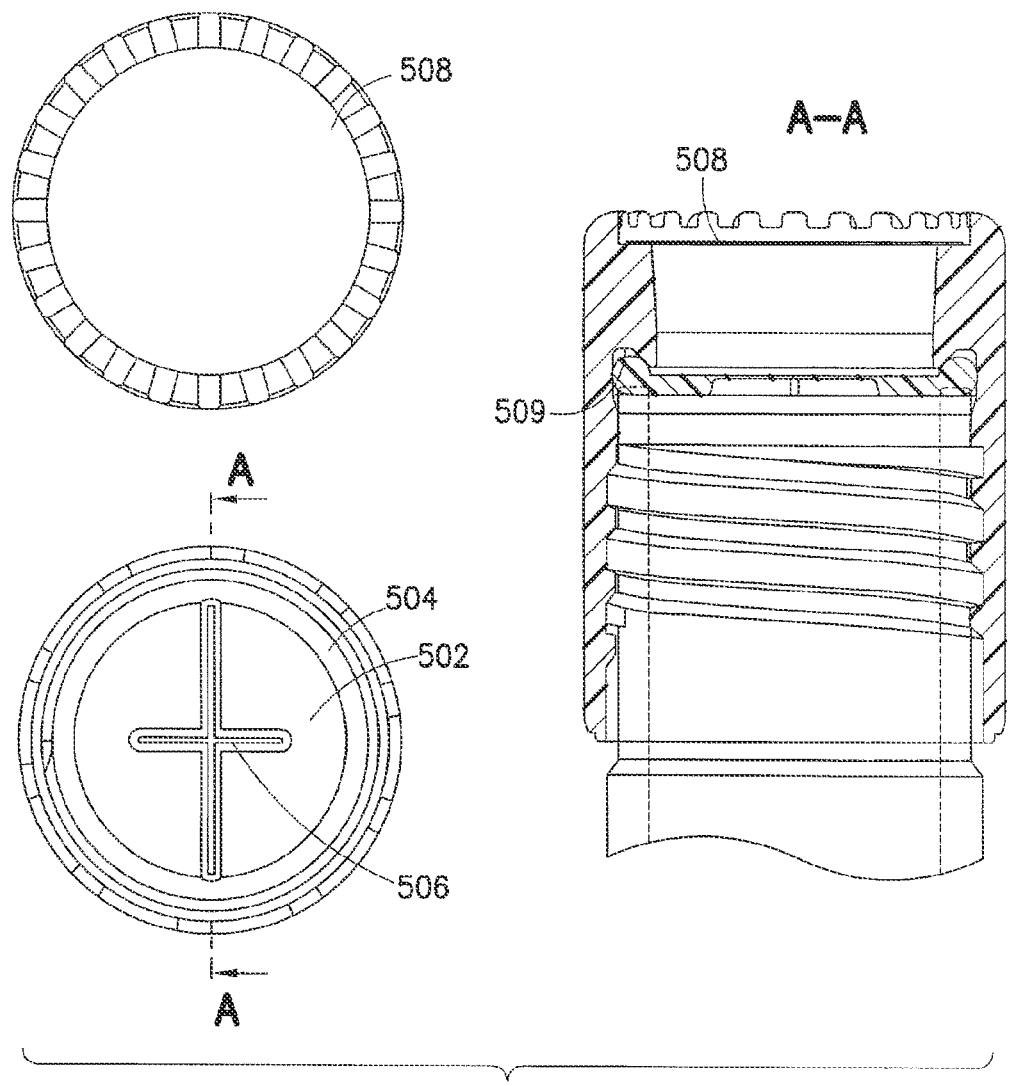
FIG. 10 is a top view and cross-sectional view of a two piece pierceable cap, having a thin webbing.

FIG. 10 illustrates a further embodiment, wherein the features illustrated by FIG. 9 may be optionally combined with an upper frangible layer, such as a foil seal 508.

In the embodiments described above, the cap may consist of at least two components, an external shell and a frangible, membrane with elastomeric properties. The external shell 501 serves to secure the membrane to the vessel. In this embodiment, the membrane 502 provides a leak-proof seal that is reinforced by the threads 505 of the shell 501.

The membrane 502 may be separate or integral with the shell. The membrane contains a pre-made, slit geometry 506 that may be sealed by a thin membrane, or web of elastomeric material 507, which may be a separate layer, or integrated within the membrane 502. The seal is ruptured through the webbed slits 506 when accessed by a transfer device. The slit geometry 506 may be symmetrical, wherein both slits are the same length, or asymmetrical (as shown) where the slits vary in length and or proportion. As demonstrated by FIGS. 9-11, in one embodiment the slit geometry 506 may appear in a configuration resembling a cross. However, the present invention is by no means limited to any particular slit orientation or slit geometry. The outline of the slit orientation may also be thickened with more material in order to guide how the thin webbing tears.

In the FIG. 9 embodiment, the cap may also be configured to receive an O-ring 504, which would fit within a recess 510 disposed on the interior surface of the shell 501. The O-ring may be integral with the shell 501, or a separate component.

This O-ring 504 functions to form a liquid tight seal between the shell 501 and the vessel 503. The seal formed by the O-ring 504 maintains sample integrity while preventing aerosolization and contamination caused by the escape of the sample contents from the vessel. It also provides a slit geometry without relying on a feature on the shell 501 to open the membrane 502, such as extensions from the shell itself. In contrast to other embodiments described herein, the membrane taught by the present embodiment may be a single frangible layer, rather than multiple layers. The two-part design allows for the control of the seal by the securing mechanism on the external shell 505.

The elastomeric material may be opened along the predetermined slit geometry 506 when accessed by the manual or automatic transfer device. As the elastomeric material used will be generally resilient and compliant, it functions to closely contact the tip of a transfer device, which drastically reduces or eliminates aerosolization and potential contamination. As the transfer device advances further into the vessel, through the slits, the slits will begin to tear, allowing for venting to occur. This venting further reduces the incidence of aerosolization and contamination. The slit geometry and webbing also increase the efficiency of any fluid pumping from the vessels themselves, as it serves to prevent the creation of a vacuum.

Figure 11:
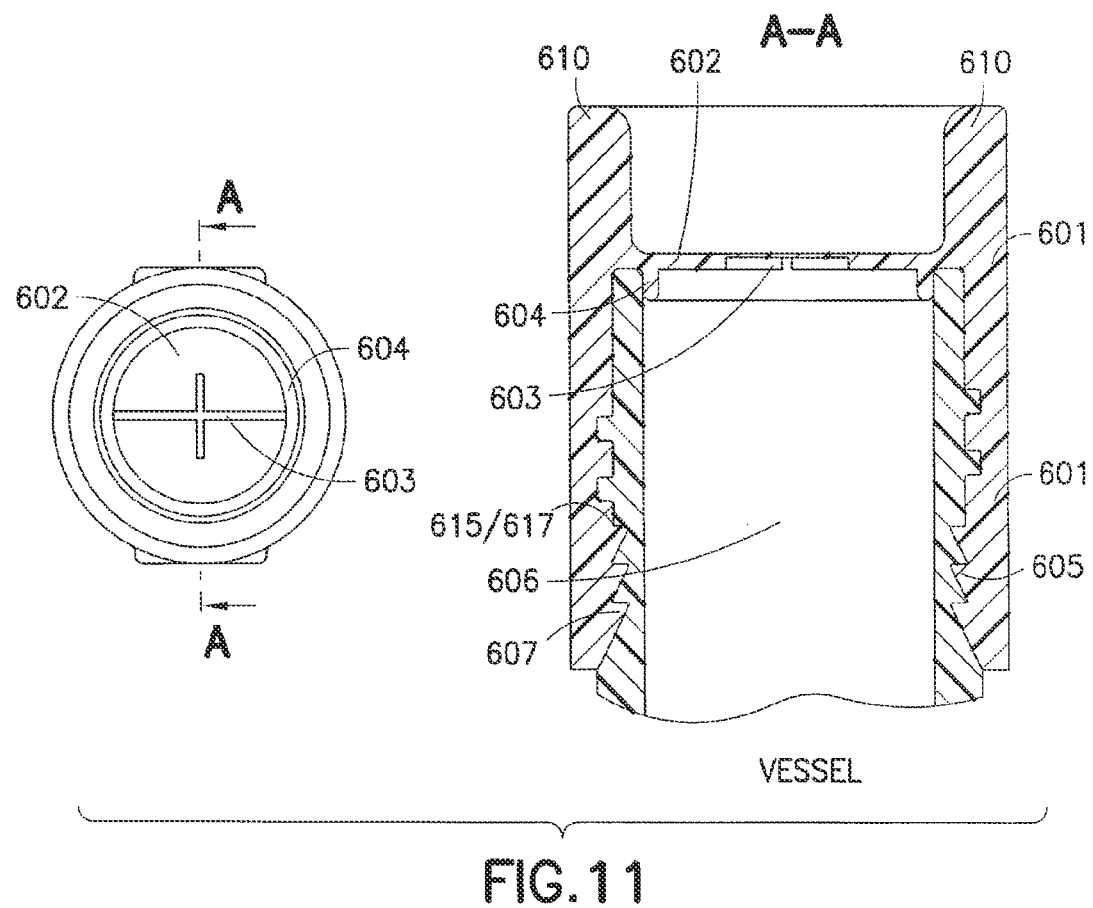
FIG. 11 is a perspective view of a pierceable cap configured to lock onto a vessel.

FIG. 11 shows another alternative embodiment of a one-piece cap with an integrated frangible membrane 602 and an O-ring 604. This embodiment is a departure from the other embodiments described herein, in that the frangible membrane 602, O-ring 604 and shell 601 are constructed as a single piece, and not separate components. The present embodiment also does not require extensions for piercing the frangible membrane 602. The one-piece locking cap of the present embodiment contains coupling structures for securing, snapping, or locking the cap to a vessel or tube ("locking structures") 605. For purposes of this disclosure, the terms "vessel" and "tube" are used interchangeably. As noted above, the frangible membrane 602 is capable of being incorporated in the assembly structures previously described.

FIG. 11 depicts a cross-section view of the single cap assembled on the vessel 606 with a bottom view of the cap. The shoulder 610 at the top of the cap prevents the user from touching the sample membrane 602 as the cap is attached to the vessel 606. The thin section 603 of the membrane 602 defines the tear geometry of the cap. The internal O-ring 604 seals to the inside of the tube and is chamfered for guiding the insertion of the cap on the vessel. As seen in FIG. 11, the O-ring 604 is configured to sit flush with the interior wall of the vessel 606. The juxtaposition of the O-ring 604 and the vessel 606 create a seal, which prevents aerosolization of the sample and therefore reduces or eliminates contamination.

In one variation, as seen in FIG. 11, the cap 601 may contain locking structures such as sawtooth or ratchet-like projections 605 on the, lower inside portions of the shell 601. A triangular "ratcheting" feature in the cap is employed wherein the "slant" portion is oriented in the direction of insertion and the flat portion 615 is oriented in the direction of removal of the cap. The flat portion 615 then contacts the ridge 617 on the vessel. The flat portion 615 of the top projection contacts the bottom surface of the corresponding recesses 607 on the vessel 606. In a preferred embodiment, there are three ridges 617 in place for seal redundancy, however, the number of ridges can vary.

While the embodiments depicted herein are described as triangular sawtooth or ratchet-like projections, the actual structure can be any type commonly known that will lock or secure the cap to the vessel, including but not limited to ridges and threads. By applying a downward axial force to the cap, a dynamic seal between the cap and the vessel is created.

This seal may be due, at least in part, to an internal expansion of the locking structures 605 that are engaged under the locking structures or recesses present on the vessel 607.

In another preferred embodiment, as depicted in FIGS. 11A and 11B, the shell 608 may be configured with at least one elastomeric ridge 608 circumferentially disposed on the inner surface of the shell 601. This ridge may be in the shape of a sawtooth structure, as described above. In this embodiment, as depicted in FIG. 11B, the elastomeric ridge(s) 608 may not mate with a corresponding structure on the sample vessel. Instead, a seal is provided between the vessel and the shell, by way of the elastomeric ridge(s) 608. In this embodiment, the outer diameter of the vessel is larger than the inner diameter of the shell. In alternate embodiments, the vessel may contain one or more annular ridges (not shown) that may be positioned above the elastomeric ridge(s) 608 of the shell, when the shell is coupled to the vessel. The annular ridges on the vessel, while not required, may further prevent the cap from being inadvertently removed from the vessel.

The embodiment of the cap depicted, for example, in FIGS. 11A and 11B, which is preferably composed of elastomeric or similarly "elastic" material is designed to possess a certain degree of elasticity. This property enables the cap to stretch or adapt to the outer diameter of the vessel. The cap described in this particular embodiment may be advantageous over a traditional "hard cap" that would require manual manipulation to place on and off. The cap of the present embodiment provides a liquid-tight seal that is maintained during handling and agitation of the vessel. The liquid in the sealed vessel may then be accessed by piercing the frangible membrane 602 of the cap. By virtue of the described locking mechanisms, the cap may be retained on the vessel even when a separation force is applied. The cap can maintain a liquid tight seal while a torsion and/or vibration force is applied to the vessel. The cap can be used as a primary cap or as a replacement cap after the contents of the vessel have been accessed on the vessel has otherwise been unsealed.

The cap is configured such that its removal is unnecessary to access the liquid in the sample. Accessing liquid can be performed manually, or by using liquid handling automation, which is an improvement over a traditional screw cap. Such handling can be performed using any of the methods known in the art, but in preferred embodiments is done using the transfer devices described herein.

The integrated frangible membrane 602 is intended to be punctured in such a way that it prevents sealing to the liquid handling apparatus, resulting in accurate manipulation of the liquid. The cap can therefore be handled without contaminating the membrane surface accessed by the liquid handling robot. The cap is easily manufactured with no assembly required.

Contamination of the integrated membrane is prevented in part, by the shoulder 610 at the top of the cap, which is smaller than the diameter of the pressure pad of the thumb or forefinger of an average user. By virtue of this design, when applying the cap by placing a downward force on the top of the cap, the user does not contact the frangible membrane 602. The elimination of this contact substantially reduces or prevents any contamination on the part of the user.

The coefficient of friction between the frangible membrane and the pipette tip is sufficient to allow a transfer device to be easily inserted into or removed from the membrane.

The manner in which the slits of the pierceable or frangible membrane tear, otherwise known as tear geometry, is an important factor for maintaining a proper liquid tight seal. The tear geometry in the present embodiment is controlled, at least in part, by a layer of membrane 603 in a precisely defined geometry that is multiple times thinner than the rest of the membrane. However, in further alternative embodiments the membrane portion 603 does not have to be thinner than the rest of the membrane 602. This membrane portion 603 may be made of exactly the same material as the rest of the membrane 602, or may be a different material. The geometry of the membrane portion 603 will define where the membrane tears when it is pierced. In one preferred embodiment, sealing around a pipette tip from a liquid handling robot is controlled by providing a cross slit geometry allowing the membrane to open in two directions. After being pierced by a transfer device, such as an automated robot, the slits close to form a liquid tight seal.

The embodiment depicted in FIG. 11 is optimized in part, by the fact that one slit is longer than the other. This configuration may further contribute to the reduction of leakage and aerosolization. The geometry functions to prevent sealing of the membrane to the pipette tip during sample access. The slit is forced to open unevenly causing air gaps along the long slit preventing a vacuum seal around the tip. This slit geometry also functions to provide venting so as to increase the pumping efficiency of fluid from the vessel, as it reduces or eliminates the creation of a vacuum within the vessel itself.

In another embodiment, the cap employs an internal O-ring 604 at the undersurface of the membrane 602 and a three-ridge redundant seal at the internal base of the cap while using a suitable elastomeric material that conforms to vessel geometries. For ease of assembly, the ridges 607 and the O-ring 604 are chamfered. The multi-surface redundant seal is present on both the inner and outer top surface of the tube, as well as below the locking structures on the tube at the pivot point of the dynamic movement of the cap on the tube during agitation.

The one-piece locking cap described herein is useful to eliminate several user steps of securing and removing screw caps on sample tubes, such as any commercially available buffer tubes. Once a sample is added to a sample vessel, the one-piece locking cap is placed on the vessel with a downward axial motion. The vessel is then agitated in a multi-tube vortex that contains a stationary plate and a movable plate with the vessel and one-piece locking cap placed between them.

Typical sample buffers for molecular diagnostics contain high levels of detergent that can both lower the surface tension of the liquid allowing for a higher incidence of leaks as well as lubricate the surface of the thermoplastic/elastomeric parts. Once agitated the sealed vessel can then be accessed by a transfer device, such as the BD MAX instrument. The instrument will pierce the integrated frangible membrane with a pipette tip causing the thin layer of webbing to tear along the cross shaped pattern allowing for tearing in multiple directions and therefore preventing sealing to the pipette tip. The one-piece locking cap is retained on the tube while the pipette tip is removed from the tube. Once removed from the tube, the integrated membrane closes, thus forming a functional liquid tight seal to prevent liquid spillage during further handling of the sample tube.

The geometry of membrane portion 603 illustrated in another embodiment is directed to a pierceable cap for a vessel that maintains a spill-proof, leak-proof, or vapor-escape proof seal during sample transport, and storage and can be accessed by a manual or automated liquid handling robot that deploys transfer devices for aspirating the sample from the vessel. This embodiment mitigates the risk of sample splashing and aerosolization when the cap is pierced by the tip of the transfer device.

In this embodiment, as illustrated in FIGS. 12-21, the cap may consist of an external shell 634 (FIG. 15), and an elastomeric seal 612. The shell and seal may be of separate or unitary construction. The seal in the present embodiment is designed to not tear upon insertion of a transfer device. Rather, the transfer device parts the walls 642 and 643, of the elastomeric seal, thus creating a space 644 without permanently tearing the elastomeric material. This space enables the transfer device to access the sample contained within the vessel.

The shell 634 (FIG. 15) may be cylindrical in shape and contain at least one outer and inner surface, which extends in an axial direction. The shell may also contain a proximal and distal opening. In such an embodiment, the distal opening may be disposed at the end which mates with a sample vessel, and the proximal opening, which may contain an access port, and may be disposed at the end which receives a sample transfer device. In preferred embodiments, the shell 634 and seal 612 are elastomeric. In alternative embodiments, the shell may be constructed from a harder material, and only the seal is elastomeric.

As illustrated in FIG. 15, the seal 612 has a diameter that is greatest where it seats into the shell 634. In one embodiment, the outermost diameter of the seal is greater in diameter than the inner wall of the shell, such that the seal is retained in the shell when the cap is not on the vessel/specimen tube, regardless of whether or not the seal is bonded or adhered to the shell.

FIG. 15 illustrates the seal 612 after it has been pierced and the transfer device removed. In the illustrated embodiment, a support band 636 illustrated in cross-section as an O-ring is disposed under the perimeter of the seal 612. The support band 636 is illustrated as a separate component but it can be monolithically integrated and be of the same material as the seal 612. Whether the support band 636 is integral to the seal or a separate component, it provides the function of sealing between the shell 634 and the mouth of the tube. The support band may contact at least three surfaces, namely the top surface of the tube, the sidewall of the shell, and the bottom surface of the shell wall or inner surface of a groove in the shell. The groove 509 (FIG. 10) in the shell retains of the seal or O-ring during penetration of the pipette tip. In further embodiments, the support band 636 may be disposed on top of the collar 623, rather than below it.

In other embodiments the seal 612 may contain an annular ring such as collar 623, and one or more ribs 620 and 621. While the embodiment depicted in FIGS. 12-15 show two ribs 620 and 621, more than two ribs may be deployed in alternative embodiments of the present technology. The seal may also contain two primary surfaces. The first surface 627 faces away from the vessel intern and receives a transfer device such as a pipette, and the second primary surface 628 extends into the sample vessel. Each rib 620, 621 may contain two peripheral walls 624 and 625. Each peripheral wall 624, 625 extends in an approximately axial direction from the collar 623. A bottom surface 626 may also connect each peripheral wall 624 and 625. Each rib also may contain at least two lateral sidewalls 629, that extends from the bottom surface 626 to the collar 623. The ribs 620 and 621 extend radially inward, and axially downward or distally from the collar 623 of the seal 612, into the vessel. The entire seal may be integrally formed by methods such as injection molding, or may be assembled separately and each individual component bonded individually. In FIG. 14, a top down perspective view of the seal 612, assembled with the shell 634 and vessel is shown.

In embodiments where the individual components of the seal are individually bonded together, the joints where the individual surfaces meet may form liquid-tight seals. However, in alternative embodiments these joints may be configured according to aspects of the present technology described herein to contain perforations or scorings to allow for additional controlled venting along these joints, upon penetration with a sample transfer device.

While FIGS. 12 and 13 depict a seal with two ribs, the seal may be configured with 1, or more ribs, and may include 2, 3, 4, 5 or 6 ribs. Variation in the number of ribs may alter the size and dimension of each rib and the tearable portion contain therein. Increasing the number of ribs may serve to increase the effectiveness of the set in guiding a transfer device into a vessel.

In the illustrated embodiment, the ribs are arranged radially, in order to achieve an intersecting angle of 90°. However, the ribs may be configured to intersect at any angle, relative to one another.

In this embodiment, the bottom surface 626 may contain a slitted portion having tearable portion(s) 630, which may be symmetrical or asymmetrical. The tearable portions 630 may be frangible and are designed to tear or puncture upon insertion of a sample transfer device. The tearable portion(s) 630 may be thinner than the rest of the seal, and may also contain a webbing integral within the seal, in accordance with the embodiments described in detail above.

The ribs 620 and 621 may extend into the vessel both vertically and horizontally. They therefore act a guide to the penetration of the transfer device so, that the tearable portions 630 are initially pierced. Being made of suitably resilient material, the initially pierced seal seats around the transfer device. As a result, any venting of the vessel that occurs during the initial pierce may be through the transfer device. As the transfer device advances through the seal, the tearable portions tear further, allowing for venting around the transfer device and through the seal during sample transfer.

Upon extraction of the transfer device, the support band, which has a circumference that may be slightly less than the outer circumference of the seal 612, exerts an upward pressure on the inwardly extending sides 620, causing them to join together and close upon the tears formed by the pierce of the transfer device. In other embodiments, the outer circumference of the support band and the outer circumference of the seal may be approximately the same.

FIGS. 16 through 21 depict another embodiment of a pierceable cap made up of at least a seal 641, and a shell 634 that combines elements to improve resealing performance. The seal may contain a slitted portion 640, which may either contain one or both of an openable portion 644, which is unjoined, or a frangible portion 645. The seal 641 and shell 634 may be coupled to form the pierceable cap. The seal 641 may include an annular ring, or projection 646 that defines the outermost surface of the seal 641, and projecting upward from the surface of the seal 641 as seen in FIG. 17. A complimentary annular protuberance 639 on the lower surface of the seal 641 is offset from the seal 641 perimeter. Further, the protuberance 639 may be positioned such that it sits between on the walls of the tube 631 and the shell 634 when assembled.

Figure 21:
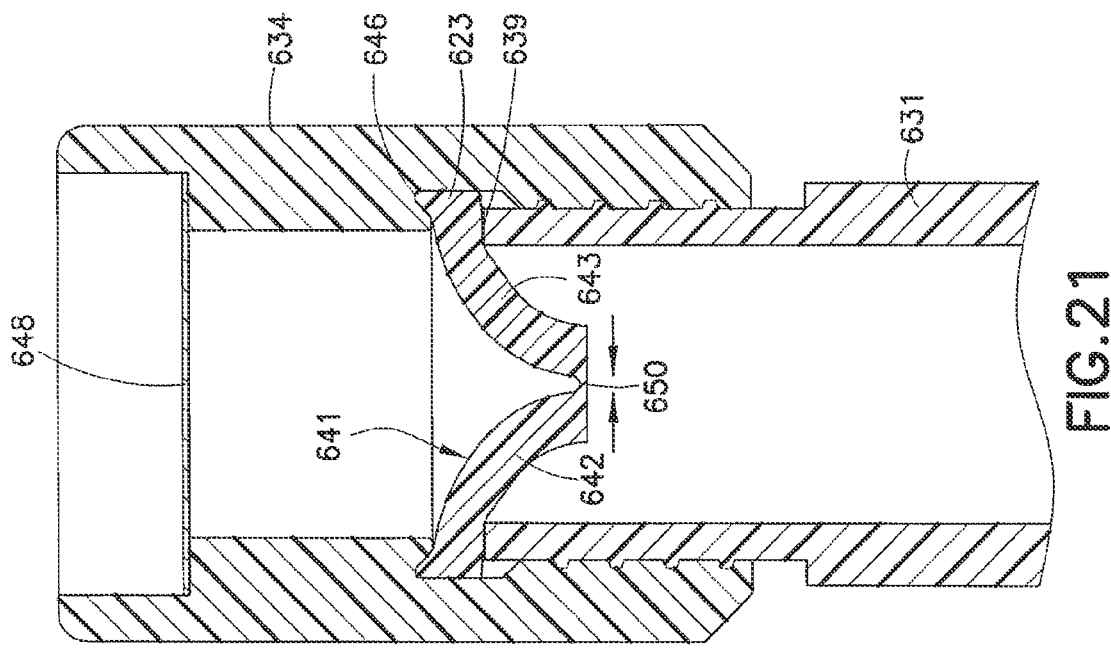
FIG. 21 is a cross section of a shell and seal prior to assembly with a sample vessel.
Figure 20:
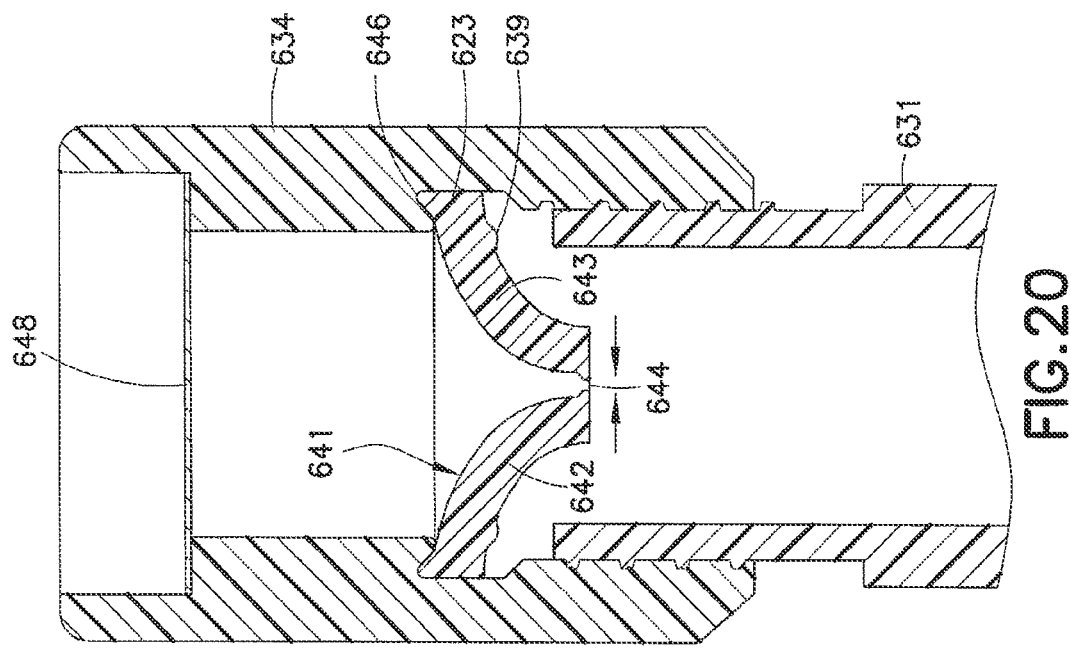
FIG. 20 is a cross section of a shell and seal assembled with a sample vessel.

FIG. 20 depicts the relationship of the cap and vessel 631, before the cap is fully screwed onto the vessel, while FIG. 21 demonstrates the structural and functional relationship after the cap has been fully screwed onto the vessel. The protuberances 639, act in concert with the walls of the vessel 631, (as depicted in FIGS. 20 and 21) to close the seal sidewalls 642 and 643 upon each other and form a seal. As shown in FIG. 21, as the cap is screwed further onto the vessel 631, internal stresses are imposed on the sidewalls 642 and 643 of the seal 641, and more particularly, on the protuberances 639. The internal stresses create forces on the sidewalls of the seal 642 and 643 that urge the sidewalls 642 and 643 toward and into contact with each other.

With the sidewalls 642 and 643 pressed upon each other in this manner to create a liquid seal, the design of the penetrable bottom portion of the seal may be accomplished in at least two possible ways. The first, as seen in FIG. 18, is an openable seal. When the seal is in its native configuration, the apex of the sidewalls 642 and 643 do not touch each other at all but are openable, and instead form a very narrow slot 644 in a slitted portion 640, just wide enough to facilitate injection molding. When assembled with the shell 634 and vessel 631, as shown in FIG. 21, the sidewalls 642 and 643 are forced together to create the seal 650. This embodiment may have the advantage of not being torn during tip insertion/penetration, thus limiting the potential for debris falling into the sample tube that may result from the tearing mechanism.

The second embodiment seen in FIG. 19 depicts a frangible seal 645 on or within the slitted portion, having a thin web of material that is torn on the first penetration of the pipette tip. In all other aspects, it performs identically to the seal described in the previous paragraph.

Both of the embodiments of the seal in FIGS. 18 and 19 may be used in conjunction with a foil top seal 648 as shown in FIG. 20, to improve durability for shipping and handling, and to serve as an additional barrier to aerosols during pipette insertion.

In certain embodiments, the seal may be made of any material which is sufficiently resilient to form a seal around the outer circumference of the transfer device, such as a pipette, when initially pierced. However, since the inwardly and downwardly sloping ribs or sidewalls mitigate the risk of aerosolization upon initial piercing, sealing around the transfer device on initial pierce may not be required. In the illustrated embodiment, the seal 612, 641 has an elastomeric membrane 614, 645. During initial piercing, the membrane 612, 645 conforms to the circumference of the transfer device in a manner to prevent the above-described unwanted splashing or aerosolization of the sample from the vessel, thereby ensuring that the sample remains contained in the vessel during the initial piercing step.

In one embodiment, the liquid transfer device is a pipette tip having a filter (not shown) contained therein. Upon insertion of the transfer device, there is a pause in its motion after piercing in order to allow any air pressure within the vessel to vent. The seal provides the leak-proof barrier and forces any venting at this stage through the transfer device and not around the transfer device.

FIG. 15 which shows the seal 612 in cross-section disposed in the vessel 521. The external shell provides the locking mechanism to the liquid vessel and ensures that the seal remains in place during storage and transport as well as protecting the seal from being damaged and therefore compromised.

In yet another embodiment of the present invention, a method is provided for advancing at least a portion of a transfer device into the access port of a shell, which is secured to a sample vessel. As the transfer device enters the access port, it is advanced distally and guided, in part, by one or more ribs. The transfer device is advanced towards the webbing contained in the bottom surface of the seal, and ultimately punctures the webbing, in order to acquire access to the sample.

Furthermore, changing the motion profile of the tip of the transfer device during penetration may reduce the likelihood of contamination. Possible changes in the motion profile include a slow pierce speed to reduce the speed of venting air. Alternative changes may include aspirating with the pipette or similar device during the initial pierce to draw liquid into the tip of the transfer device.

FIG. 22A illustrates a septum 700 according to one embodiment of the invention. Although described as a separate embodiment, the septum 700 can be inserted in place of the frangible layers described herein, the membrane described herein and the elastomeric shield described herein. The frangible layers are illustrated as frangible layer 15 in FIGS. 1A-1G and FIGS. 2A-2B; frangible layer 75 in FIGS. 3A-3G, frangible layer 95 in FIGS. 4A-4B. Frangible layer 105 in FIGS. 5A-5B, frangible layer 215 in FIGS. 6A-6E, frangible layer 315 in FIGS. 7A-7C and frangible layer 415 in FIGS. 8A-8E. The membrane layers are 502 in FIGS. 9 and 602 in FIG. 11. The elastomeric shield is illustrated as 612 in FIGS. 12-21. The septum has a collar or lip 705. The collar or lip 705 has a barb 710. The septum also has indentations 715 that define the inner walls of the septum. As illustrated, the indentations 715 are shaped like a pointed arch. Because the pointed arch extends both radially and inwardly, the point arch defines a half-dome indentation.

The barb 710 is a septum feature that holds the septum in the cap 720 when the cap is not on the tube 730. The barb 710 is elastomeric and sufficiently flexible to be forced through a narrower inner diameter portion 735 of the cap 720. The cap 720 and tube 730 are illustrated in FIG. 22B. The septum barb 710 is deflected during insertion but then extends into a wider inner diameter portion 740 of the cap 730. Once inserted, the barb 710 is retained in the wider diameter portion of the cap 730. This is illustrated in FIGS. 22C and FIG. 22D. The barb 710 is resilient and deforms into the cap 720 but does not extend into the cap. This is illustrated in FIG. 22E. The retention of the barb 710 in the wider inner diameter portion 740 of the cap 720 maintains the planarity of septum seal and the slit region of the septum seal relative to the top 745 of cap 720 and the top 750 of the tube 730.

The cap undercut 755 therefore has the wider inner diameter portion 740 the accommodates the barb 710, the narrower inner diameter portion 735 retains the septum 700 in the cap 720 and a transition angle 760 that maintains a coplanar relationship of the septum surfaces with cap 720.

FIG. 22F illustrates how the septum 700 of FIG. 22A seats in the cap of FIG. 22B. The septum collar 705 has a vertically extending protrusion 765. This protrusion 765 sits in a gap 770 in a laterally extending surface of the cap 720. That surface 775 extends from the cap wall 780 inward. The gap 770 is defined by the cap wall 780 on one side a rib 785 on the other.

Septum collar 705 interfaces with rib 785 to prevent the septum 700 from being pushed into tube 730 when a pipette (not shown) is inserted through septum 700 to access sample in the tube 730. Because the collar protrusion 765 is retained in the gap 770, additional deflection of the protrusion 765 would be required to push or pull the septum 700 from its installed position during sample access. The structure in FIG. 22F reduces axial misalignment of the cap 720 and the tube 730 by localizing deflection of septum 700 when the cap is placed on the tube.

FIG. 23A is a perspective view of the septum 700 in FIG. 22 A. The septum 700 has four half dome structures 785 that rest on the septum floor 790 and rise upwardly and inwardly toward in interior wall 795 of the septum 700. Each half dome structure 785 has two curved triangular faces 800 that share an arched boundary 805. The intersection of the faces 800 with the interior wall 795 of the septum 700 forms a pointed arch 810. The arched boundary 805 is a half arch trajectory. The dome shape aids in re-closure of the septum so that tube will not leak after the pipette has been retracted from the septum. Also, the dome shape provides a structure that resists inversion of the septum during sample handling steps such as pipette tip withdrawal and thermal cycling. The dome shaped structure reduces insertion and extraction forces by deflecting the material rather than stretching.

FIG. 23B is detail view of a cross section of the septum arch illustrated in FIG. 23 A. FIG. 23A illustrates the arched boundary 805 of one-half dome structure 785 in relation to the septum floor 790 and the septum interior wall 795.

Figure 24:
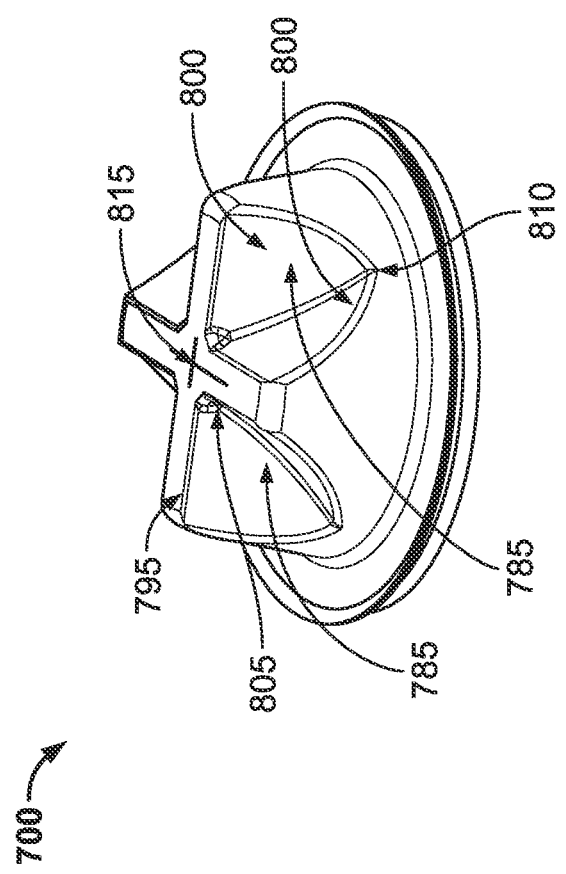
FIG. 24 is a bottom view of one embodiment of the septum described herein.

FIG. 24 is a bottom view of one embodiment of the septum described herein. The floor 795 of the septum 700 (which contains a weakened portion 815) separates the four-half dome shaped indentations 785. The pointed arch 810 is seen from the back as are triangular faces 800 and arched boundary 805. The pointed arched portion 810 extends along the perimeter of the septum and the arched boundary 805 extends inward toward the center of the septum. As illustrated, the lateral extent of the weakened portion (e.g. the scored portion or slit that extends only partially through the thickness of the septum floor 795) is such that the weakened portion does not traverse the entire extent of the floor 795.

Figure 25:
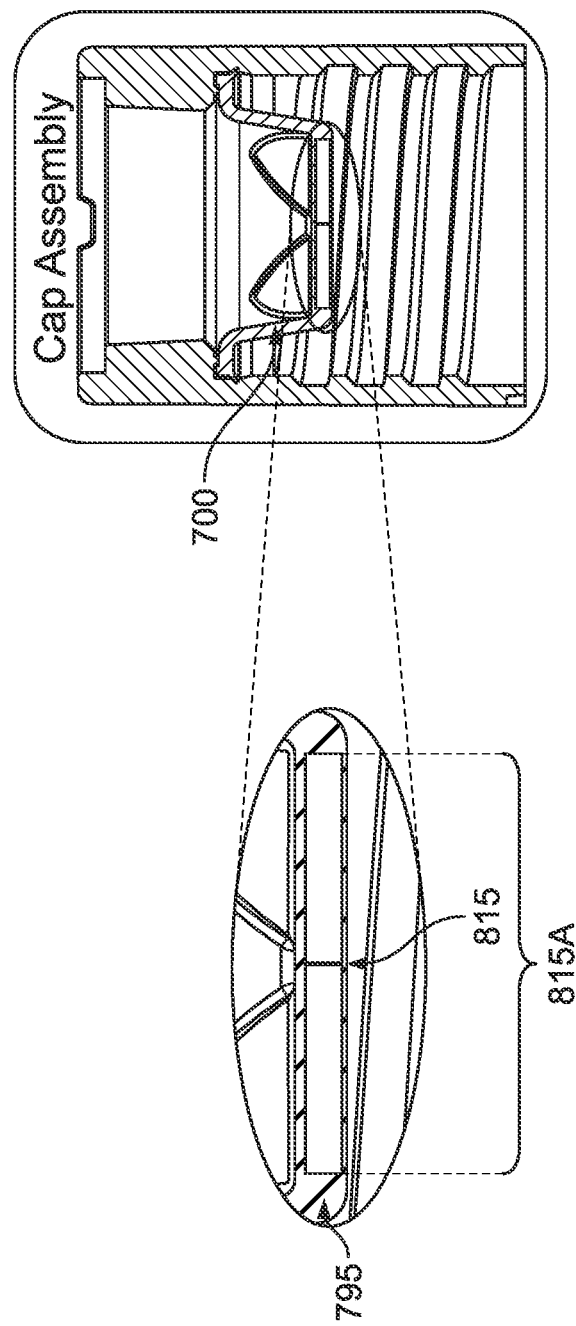
FIG. 25 is a cross section of the septum showing the weakened portion in the bottom thereof.

FIG. 25 is a detail cross section of the septum 700 showing the weakened portion 815 in the septum floor 795. Note that the weakened portion in this embodiment is a slit that extends approximately half way through the thickness of the septum floor 795. Also, in this embodiment, the slit 815 traverses almost the entire length of the floor. This is illustrated by the extent of cross slit 815A, which is illustrated lengthwise and that intersects with slit 815 which extends approximately perpendicular to slit 815A. The lateral extent of the slitted or scored portion 815 in this example is the same as the lateral extent of the tearable portion 630 illustrated in FIG. 12. FIG. 25 also illustrates that the slit 815 extends from the bottom surface of the septum floor (i.e. the surface facing into the tube) upward through some portion of the thickness of the septum floor, but not entirely through that thickness. Because the slit or weakened portion is only in the bottom portion of the septum floor thickness, the septum is able to maintain a seal even when the contents of the vessel in which the septum is placed is under pressure. In operation, this allows the pipette tip, when piercing the septum from above, to place a higher tensile stress on the septum. As the pipette tip propagates through the septum floor, the bending moment of the septum floor changes and a lower force is required for the pipette tip to propagate through the slitted portion. As noted above, the dome structures reduce insertion and extraction forces by deflecting the material rather than stretching.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A pierceable cap comprising:
a shell,
an access port in the shell adapted to allow passage of at least part of a transfer device through the access port;
a septum seal comprising a collar and a plurality of half-domed indentations extending from a perimeter of the septum toward the center thereof, wherein the indentations extend inwardly and downwardly toward a septum floor, the septum floor having a thickness, wherein the shell is adapted to receive the septum seal; and
wherein the septum floor has a slitted portion that extends only partially through the thickness of the septum floor, wherein the collar has a barb portion that extends laterally from the collar toward an interior wall of the shell that receives the septum, wherein the shell has a wider interior diameter portion and a narrower interior diameter portion and a transition portion and wherein, when the septum seal is inserted into the shell, the barb extends into the transition portion above the narrower interior diameter portion and is held into position in the shell thereby.

2. The pierceable cap of claim 1, wherein the shell is elastomeric.

3. The pierceable cap of claim 1, wherein the septum floor is substantially planar.

4. The pierceable cap of claim 1, comprising four half-domed indentations, each indentation placed in a quadrant of the septum defined by the septum floor and a perimeter of the septum.

5. The septum of claim 4, wherein the septum floor has a first portion having a length that extends along a first diameter of the septum and a second portion having the same length that extends along a second diameter, wherein the first and second portions intersect to define the quadrants.

6. The septum of claim 5, wherein a first slit extends along a portion of the length of the first portion of the septum floor and a second slit extends along a portion of the length of the second portion of the septum floor and wherein the first slit intersects the second slit.

7. The septum of claim 6, wherein the first slit has a first length and the second slit has a second length and the first length is longer than the second length.

8. The septum of claim 7, wherein the first slit has a first length that extends less than half the length of the first portion of the septum floor and the second slit has a second length that extends more than one half the length of the second portion of the septum floor.

9. The septum of claim 6, wherein the first slit has a first length and the second slit has a second length and the first length is about equal to the second length.

10. The septum of claim 9, wherein the first slit has a first length that extends more than one-half the length of the first portion of the septum floor and the second slit has a second length that extends more than one-half the length of the second portion of the septum floor.

11. The pierceable cap of claim 1, wherein the collar further comprises an upwardly extending portion at its perimeter proximate to the barb portion.

12. The pierceable cap of claim 11, wherein shell has an interior wall, wherein the shell has a laterally extending surface from the wider interior portion, wherein the laterally extending surface has a retaining rib that extends from the laterally extending surface and defines a gap between the interior wall of the shell and the retaining rib, and wherein the upwardly extending portion from the septum collar fits into the gap when the septum is inserted into the shell.

13. A method for piercing a septum comprising:
obtaining a vessel with a pierceable cap thereon, the cap comprising:
a shell,
an access port in the shell adapted to allow passage of at least part of a transfer device through the access port;
a septum seal comprising a collar and a plurality of half-domed indentations extending from a perimeter of the septum toward the center thereof, wherein the indentations extend inwardly and downwardly toward a septum floor, the septum floor having a thickness, wherein the shell is adapted to receive the septum seal and wherein the septum floor has a slitted portion that extends only partially through the thickness of the septum floor, and wherein the collar has a barb portion that extends laterally from the collar toward an interior wall of the shell that receives the septum, wherein the shell has a wider interior diameter portion that allows the barb to extend laterally and a narrower interior diameter portion that deflects the barb upon entry into the narrower interior portion and a transition portion and wherein, when the septum seal is inserted into the shell, the barb is initially deflected and then extends laterally into the transition portion above the narrower interior diameter portion as the septum seal is advanced into the shell;
positioning a pipette tip over the septum seal;
advancing the pipette tip into contact with the septum floor; and
further advancing the pipette tip through the septum floor such that the pipette tip advances through an unslitted portion in the septum floor thickness initially and then further advances through the slitted portion.

14. The method of claim 13, wherein the access port further comprises a first frangible layer positioned in the access port, the method further comprising advancing the pipette tip through the frangible layer before the pipette tip is advanced through the septum floor.

15. The method of claim 14, wherein the pipette tip is in fluid communication with an interior of the vessel after being advanced through the septum floor.

16. The method of claim 15, further comprising aspirating at least a portion of a sample in the vessel with the pipette tip after the pipette tip has been advanced through the septum floor.

17. The method of, claim 16, further comprising withdrawing the pipette tip from the vessel and through the-septum wherein the septum closes after the pipette tip is withdrawn therefrom.

18. The method of claim 15, further comprising dispensing a liquid into the vessel through the pipette tip after the pipette tip has been advanced through the septum floor.

19. The method of claim 18, further comprising withdrawing the pipette tip from the vessel and through the septum wherein the septum closes after the pipette tip is withdrawn therefrom.

* * * * *